(12) United States Patent
Galloway

(10) Patent No.: US 8,273,313 B2
(45) Date of Patent: Sep. 25, 2012

(54) SYSTEM FOR PRODUCING METHACRYLIC ACID

(75) Inventor: Frederick Merrill Galloway, Tomball, TX (US)

(73) Assignee: Saudi Basic Industries Corporation (SA)

( * ) Notice: Subject to any disclaimer, the term of this patent is extended or adjusted under 35 U.S.C. 154(b) by 0 days.

(21) Appl. No.: 12/853,045

(22) Filed: Aug. 9, 2010

(65) Prior Publication Data

US 2011/0311405 A1    Dec. 22, 2011

Related U.S. Application Data

(62) Division of application No. 11/706,800, filed on Feb. 14, 2007, now Pat. No. 7,799,946.

(51) Int. Cl.
| | |
|---|---|
| B01J 8/04 | (2006.01) |
| B01J 8/00 | (2006.01) |
| B01J 19/00 | (2006.01) |
| C07C 61/00 | (2006.01) |
| C07C 61/08 | (2006.01) |
| C07C 51/16 | (2006.01) |
| C07C 51/31 | (2006.01) |
| C07C 53/00 | (2006.01) |
| C07C 57/00 | (2006.01) |
| C07C 57/02 | (2006.01) |
| C07C 57/18 | (2006.01) |
| C07C 47/00 | (2006.01) |
| C07C 47/02 | (2006.01) |
| C07C 45/00 | (2006.01) |

(52) U.S. Cl. ........ 422/608; 422/129; 422/187; 422/600; 562/400; 562/512; 562/523; 562/542; 562/544; 562/545; 562/598; 562/600; 568/420; 568/448; 568/449; 568/470; 568/475; 568/476; 568/492

(58) Field of Classification Search .................. 422/129, 422/187, 600, 608; 562/400, 512, 523, 542, 562/544, 545, 598, 600; 568/300, 420, 448, 568/449, 470, 475, 476, 492
See application file for complete search history.

(56) References Cited

U.S. PATENT DOCUMENTS

| | | | | |
|---|---|---|---|---|
| 4,147,721 | A * | 4/1979 | Leacock | 562/532 |
| 4,234,519 | A * | 11/1980 | Yeoman et al. | 568/492 |
| 4,294,665 | A * | 10/1981 | Issei et al. | 203/50 |
| 6,409,886 | B1 * | 6/2002 | Matsumoto et al. | 203/8 |
| 2003/0233014 | A1 * | 12/2003 | Chun et al. | 562/535 |

* cited by examiner

*Primary Examiner* — Walter D Griffin
*Assistant Examiner* — Natasha Young
(74) *Attorney, Agent, or Firm* — Robert W Strozier

(57) ABSTRACT

A system and process for separating methacrolein (MA) from methacrylic acid (MAA) and acetic acid in the gas phase product from partial oxidation of isobutylene (IB) in two oxidation steps is disclosed. The process and system maximize recovery of all three components at minimum capital and energy cost, under conditions that minimize polymerization conditions and plugging by solids deposition in compressors, columns, etc.

12 Claims, 5 Drawing Sheets

SYSTEM FOR PRODUCING METHACRYLIC ACID

RELATED APPLICATIONS

This application claims the benefit and priority as a divisional application to U.S. patent application Ser. No. 11/706,800, filed 14 Feb. 2007 (02/14/2007 or 14.02.1.2007).

BACKGROUND OF THE INVENTION

1. Field of the Invention

The present invention relates to a method and system for the partial oxidation of isobutene having reduced methacrolein, methacrylic acid and acetic acid losses.

More particularly, the present invention relates to methods and systems for the partial oxidation of isobutene including the steps partially oxidizing an isobutene stream into a crude methacrylic acid containing stream in an oxidation subsystem. The crude methacrylic acid containing stream is instantaneously or near instantaneously quenched with a sufficient amount of a recycle stream in a sump portion of a quench column of a quench/distillation subsystem, sending a first portion of a bottoms product for methacrylic acid and acetic acid separation and purification, recycling a second and major portion of the bottoms product as the recycle stream to quench the crude methacrylic acid containing stream, sending a portion of an overhead product from the quench/distillation subsystem to a methacrolein recovery or absorber/stripper subsystem, recycling a major portion of the bottom stream from the stripper column to an upper portion of the absorber column and forwarding a recovered methacrolein stream from the overhead of the stripper column to the oxidation subsystem.

2. Description of the Related Art

Many patents and publications disclose aspects of a process of partially oxidizing isobutene or an isobutene equivalent into methacrylic acid in a single step or multi-step oxidation process. Some of these patents related directly to or extensively discuss quenching of the effluent from the partial oxidation of the isobutene or isobutene equivalent input stream.

In U.S. Pat. No. 4,554,054 disclosed a process to recover acrylic acid or methacrylic acid by using a split quench process which allows acrylic acid or methacrylic acid to be recovered from the resulting aqueous solutions by a combination of solvent extraction and azeotropic dehydration that minimizes the amount of solvent required.

In U.S. Pat. No. 4,618,709 disclosed a process for separation of methacrylic acid from a methacrylic acid-containing, gaseous reaction mixture obtained by subjecting methacrolein or a compound which can afford methacrolein under reaction conditions and molecular oxygen to gas phase reaction in the presence of a catalyst for oxidation under the coexistence of an inert gas for dilution which comprises (a) cooling the gaseous reaction mixture from a reactor wherein the gas phase reaction has been effected to separate into condensable components including methacrylic acid, acetic acid and water vapor as a condensed liquor and non-condensable components including methacrolein as anon-condensed gaseous mixture, (b) eliminating contaminating methacrolein from the condensed liquor and (c) contacting the resulting condensed liquor with an organic solvent to extract methacrylic acid, followed by separation into an organic solvent solution including methacrylic acid and an aqueous solution as waste water, characterized in that (1) the inert gas for dilution is a non-condensable gas or its mixture with water vapor and (2) the aqueous solution ultimately separated is evaporated and the evolved vapor is subjected to catalytic combustion with molecular oxygen, whereby the amount of waste water to be discharged is much suppressed.

In U.S. Pat. No. 4,925,981 disclosed a method of isolating and recovering methacrylic acid from a methacrylic acid-containing reaction product gas resulting from the vapor-phase catalytic oxidation of isobutylene, tertiary butanol or isobutyraldehyde, which comprises introducing the reaction product gas comprising methacrylic acid and various by-products including high boiling substances at a high temperature of 250° to 300° C. into a cooling zone, rapidly cooling the gas therein to a temperature of not more than 100° C. to condense methacrylic acid and thus isolate methacrylic acid, while also converting the high boiling substances to fumes, thereafter introducing the cooled gas containing said fumes into a venturi scrubber, contacting it therein with an aqueous medium to remove said fumes, finally introducing the treated gas into a methacrylic acid-absorbing zone and absorbing methacrylic acid by absorption into an aqueous medium.

In U.S. Pat. No. 4,956,493 disclosed a process for producing a methacrylic ester which comprises catalytically oxidizing isobutylene, tert-butanol, methacrolein or isobutyl aldehyde in a vapor phase; removing light-boiling substances form the resulting reaction product by distillation or stripping; extracting methacrylic acid from the resulting methacrylic acid aqueous solution using a saturated chain aliphatic hydrocarbon having 6 to 9 carbon atoms as a solvent; recovering the solvent from the obtained solvent solution of methacrylic acid; esterifying the resulting methacrylic acid by the reaction of it with a lower aliphatic alcohol or a lower alicyclic alcohol having 1 to 12 carbon atoms using a porous strongly acidic cation exchange resin as a catalyst for esterification; and then subjecting the thus obtained esterification reaction product to a purification step.

In U.S. Pat. No. 4,987,252 disclosed in order to recover methacrolein and/or methacrylic acid by quenching a reaction product gas obtained by catalytic oxidation of isobutylene or the like, the reaction product gas is charged into a quench column through a double-wall pipe and is then brought into contact with a condensate as a cooling medium. Deposition of terephthalic acid and the like inside the column is prevented by controlling the temperature of a bottom in the quench column and that of an overhead gas of a quench column unit. An aromatic carboxylic acid, aromatic aldehyde, metal powder is added to an aqueous solution of methacrylic acid, which contains terephthalic acid and the like, so that the terephthalic acid and the like are caused to precipitate for their removal.

In U.S. Pat. No. 5,356,460 disclosed methacrolein is removed from a gaseous mixture by absorption by means of an aqueous solution which contains from 60 to 90% by weight of methacrylic acid.

In U.S. Pat. No. 5,780,679 disclosed a process for the separation of (meth)acrylic acid from the reaction gas mixture formed in the catalytic gas phase oxidation by counter-current absorption using a high-boiling inert hydrophobic organic liquid, in which the reaction gas mixture is passed through an absorption column countercurrently to the descending high-boiling inert hydrophobic organic liquid and (meth)acrylic acid is subsequently fractionally separated from the liquid effluent leaving the absorption column and containing (meth)acrylic acid, wherein a rectifying process is superimposed on the absorption process occurring naturally in the absorption column by removing a quantity of energy from the absorption column which exceeds its natural energy loss resulting from contact with the ambient atmosphere.

In European Patent No. 0345083 B1 disclosed a process for recovering methacrolein which comprises: a reaction step (A) comprising catalytically oxidizing isobutylene, t-butanol, methacrolein, isobutyl aldehyde or isobutyric acid or a mixture thereof with a gas containing molecular oxygen in a vapor phase, a methacrylic acid condensation step (B) comprising contacting the reaction product gas obtained in step (A) with an aqueous phase containing methacrylic acid and acetic acid to obtain an aqueous solution of methacrylic acid, a methacrylic acid extraction step (C) comprising extracting methacrylic acid (page 24, lines 11 and 12) obtained in step (B) with an extraction solvent which is a saturated hydrocarbon having 6 to 9 carbon atoms, and separating the extracted methacrylic acid to a solvent phase and an aqueous phase containing acetic acid, a methacrolein recovery step (D) comprising contacting the gas containing methacrolein and methacrylic acid discharged from step (B) with an aqueous phase containing methacrylic acid and acetic acid to recover methacrolein and methacrylic acid contained in said gas into said aqueous phase, a methacrolein desorption step (E) comprising contacting the aqueous phase containing methacrylic acid, acetic acid and methacrolein discharged from step (D) with a gas containing molecular oxygen to desorb methacrolein, and a methacrylic acid recovery step (F) comprising contacting the gas containing methacrylic acid and methacrolein desorbed from step (E) with an aqueous phase containing acetic acid to obtain a gas containing methacrolein, at the same time recovering methacrylic acid into said aqueous phase, which process comprises circulating the aqueous phase containing acetic acid discharged from the methacrylic acid extraction step (C) in the methacrylic acid recovery step (F), circulating the aqueous phase containing methacrylic acid and acetic acid discharged from the methacrolein desorption step (E) in the methacrylic acid condensation step (B) and/or the methacrolein recovery step (D) and circulating the gas containing methacrolein discharged from the methacrylic acid recovery step (F) in the reaction step (A).

Although these patents and publications disclose many different processes and equipment for achieving a rapid quenching and processing of the oxidation effluent, there is still a need in the art for a system and a related process that rapidly quenches the oxidized effluent while achieving reduced methacrolein, methacrylic acid and acetic acid losses.

SUMMARY OF THE INVENTION

The present invention provides a methacrylic acid production system including an oxidation subsystem designed to oxidize isobutene into a hot oxidized stream including methacrolein (MA), methacrylic acid (MAA) and acetic acid (AA). The system also includes a quench/distillation subsystem designed to rapidly (instantaneously or near instantaneously) quench the hot oxidized stream with a sufficient amount of a recycle stream to reduce the temperature of the hot oxidized stream to a temperature below about 75° C. and to separate the oxidized stream into an MAA rich bottoms stream and an overhead stream, where the MAA rich bottoms stream is separated into the recycle stream and an MAA product stream. The MAA rich bottoms stream will also include most of the AA produced in the system, where the term most means that the MAA bottoms stream includes a least about 90% of the AA produced in the system. In certain embodiments, the MAA rich bottoms stream includes at least about 92.5% of the AA produced in the system. In other embodiments, the MAA bottoms stream includes at least about 95% of the AA produced in the system. The system also includes an absorber/stripper subsystem designed to remove unconverted MA for recycle to the oxidation subsystem and to produce absorber stream and a second MAA rich stream, which in combined with the MAA product stream. The system can also include a stripper gas subsystem for incinerating absorber column overheads into a stripper gas stream used in a stripper column to strip unreacted MA for recycle to the oxidation subsystem. The term near instantaneously or virtually instantaneously means that the recycle stream is sufficient to reduce the temperature of the hot oxidized stream to a temperatures below about 75° C. within a time span of less than or equal to 10 seconds. In certain embodiments, the time span is less than to 5 seconds. In other embodiments, the time span is less than to 3 seconds. In certain embodiments, the time span is between about 2 and 3 seconds.

The present invention also provides a quench column for quenching a hot oxidized effluent stream including a quench column having a sump section. In the sump section, the effluent stream is injected into the quench column above a liquid layer therein through a inlet. Just above the effluent inlet, a recycle stream is injected into the distillation via a recycle inlet, which is generally a spray type apparatus. The effluent stream has a temperature at or above about 200° C. and the recycle stream has a temperature at or below about 100° C. The flow rates of the two streams are adjusted so that all or substantially all of the effluent stream is reduced from its high temperature to the recycle stream temperature very rapidly, instantaneously or near instantaneously. In certain embodiments, the effluent stream has a temperature at or above about 225° C. and the recycle stream has a temperature of about 70° C., and the flow rate are adjusted so that all or substantially all of the effluent stream is reduced from its high temperature to the recycle stream temperature very rapidly, instantaneously or near instantaneously. In certain embodiments, the effluent stream has a temperature at or above about 250° C. and the recycle stream has a temperature below about 70° C., and the flow rate are adjusted so that all or substantially all of the effluent stream is reduced from its high temperature to the recycle stream temperature very rapidly, instantaneously or near instantaneously. Stated another way, the flow rate of the recycle stream and the flow rate of the effluent stream are adjusted so that the flow rate of the recycle stream is sufficient greater than the flow rate of the effluent stream to instantaneously or near instantaneously drop the temperature of the effluent stream to the temperature of the recycle stream in a sump zone of the quench column of the quench/distillation apparatus. The quench/distillation also includes an overhead processing section that produces an MA rich stream and a liquid stream that is injected into a top inlet of the quench column of the quench/distillation apparatus to improve MA, MAA and AA separation efficiency in the quench/distillation apparatus.

The present invention also provides an absorber/stripper apparatus having improved MA recovery for further partial oxidation. The absorber/stripper apparatus includes an absorber column and a stripper column. The absorber column takes a vapor fraction stream from a quench/distillation system as an input stream into a bottom section of the absorber column, which is absorbed by two MAA rich stripper derived streams having different temperatures and introduced into an upper and a top inlet of the absorber column. The streams, absorber column size and conditions are adjusted so that the overhead stream is substantially free of MA, MAA and AA and the bottoms stream includes substantially all of the MA, MAA and AA in the vapor fraction stream. The absorber bottoms are introduced into a top inlet of a stripper column where it is mixed with an upcoming stripper gas introduced into a lower section of the stripper column. The stripper column also includes a reboiler, where a portion of a bottoms from the stripper column is heated and injected into a bottom inlet of the stripper column. The streams, stripper column size and column conditions are adjusted so that substantially all of the MA is taken as an overhead stream and the remainder of the bottoms from the stripper column make up the absorber streams, while another portion is combined with a MAA/AA rich stream for MAA/AA separation and purification.

The present invention also provides a methacrylic acid production system including an oxidation subsystem designed to oxidize isobutene into a hot oxidized stream including methacrolein (MA), methacrylic acid (MAA) and acetic acid (AA). The system also includes a quench and primary distillation subsystem designed to rapidly quench the hot oxidized stream with a sufficient amount of a recycle stream and to separate the oxidized stream into an MAA rich bottoms stream and an MA rich overhead stream. The MAA rich bottoms stream is divided into at least two streams, the recycle stream and an MAA product stream, where the recycle stream is forwarded to a sump portion of the primary distillation subsystem to quench the hot oxidized stream. The overhead stream is divided into an overhead MAA rich recycle stream and a stream containing essentially all the unconverted MA, where the overhead recycle stream is forwarded to an upper portion of the primary distillation subsystem. The system also includes a stripper and absorber subsystem designed to remove unconverted MA for recycle to the oxidation subsystem and to produce a second MAA rich stream, which is combined with the MAA product stream. Optionally, a third portion of the MAA rich bottoms stream is combined with the overhead recycle stream prior to forwarding the stream to the upper portion of the distillation subsystem.

The present invention provides a method for making methacrylic acid (MAA) from isobutene (IB) including the step of oxidizing IB in the presence of oxygen and at least one oxidation catalyst to produce a hot oxidized stream comprising methacrolein (MA), MAA and acetic acid (AA). The hot oxidized stream is then feed into a sump portion a quench column of a quench and distillation subsystem of an MA production system. The hot oxidized stream is mixed with a large excess amount of a recycle bottoms stream sufficient to rapidly reduce a temperature of the hot oxidized stream to a temperature at or below about 70° C. The quench column also separates the oxidized stream into an MAA rich bottoms stream and an MAA lean overhead stream. The MAA rich bottoms stream is divided into an MAA product stream and the recycle bottoms stream. The MAA lean or MA rich overhead stream is divided into an MA recovery stream and an overhead recycle stream. The MA recovery stream is forwarded to a stripper/absorber subsystem, while the overhead recycle stream is forwarded to an upper portion of the quench column. Optionally, the overhead recycle stream is combined with a portion of the recycle bottoms stream prior to being forwarded to the upper portion of the quench column. The MA recovery stream is feed as a gaseous stream into a bottom portion of an absorber column, which is absorbed into a liquid in the absorber. An absorber bottoms stream is forwarded to a top of a stripper column, while an absorber overhead stream is forwarded to an incinerator to form a stripper gas stream a portion of which is forwarded to a bottom portion of the stripper column. A stripper overhead stream, which is rich in MA, is sent back to the oxidization subsystem for further oxidation to MA. A portion of a stripper bottoms stream is forwarded through a reboiler and recycled back to the bottom portion of the stripper column. Another portion of the stripper bottoms stream is forwarded to a surge tank to adjust stripper/absorber stream flows. A stripper bottoms stream from the surge tank is pressurized and a portion is combined with the MAA product stream and a second portion is cooled. A first portion of the cooled stripper bottom stream is forwarded to an upper port of the absorber column, while a second portion of the cooled stripper bottom stream is forwarded to a top port of the absorber column.

The present invention provides a method for quenching a hot crude methacrylic acid stream including the step of quenching the crude methacrylic acid stream in a quench and primary distillation subsystem designed to rapidly quench the hot oxidized stream with a sufficient amount of a recycle stream and to separate the oxidized stream into an MAA rich bottoms stream and an MA rich overhead stream. The MAA rich bottoms stream is divided into at least two streams, the recycle stream and an MAA product stream, where the recycle stream is forwarded to a sump portion of the primary distillation subsystem to quench the hot oxidized stream. The overhead stream is divided into an overhead MAA rich recycle stream and a stream containing essentially all the MA, where the overhead recycle stream is forwarded to an upper portion of the primary distillation subsystem. The system also includes a stripper and absorber subsystem designed to remove unconverted MA for recycle to the oxidation subsystem and to produce a second MAA rich stream, which is combined with the MAA product stream. Optionally, a third portion of the MAA rich bottoms stream is combined with the overhead recycle stream prior to forwarding the stream to the upper portion of the distillation subsystem.

The present invention further provides a process of separation including the step of introducing a hot stream comprising methacrolein (MA), methacrylic acid (MAA) and acetic acid (AA) into a quench column at a feed port. After introduction, a bottoms stream is withdrawn from a bottom port of the quench column. A first portion of the bottoms stream is introduced into the quench column above the feed port to quench the hot stream substantially instantaneously. A second portion of the bottoms stream is introduced to a top of the quench column, while a third portion of the bottoms stream is withdrawn as a MAA product stream. The process is controlled such that (1) a first mass ratio of the first portion of the bottoms stream to the hot stream is at least 5:1, (2) a second mass ratio of the first portion of the bottoms stream to the second portion of the bottoms stream is at least 5:1, and (3) a temperature of the quench stream is at or below about 75° C.

The present invention further provides a quench column apparatus including a quench column. The quench column includes: (1) a feed port for introducing a hot stream comprising methacrolein (MA), methacrylic acid (MAA) and acetic acid (AA) into the quench column, where the feed port is located above a liquid level in the quench column, (2) a bottom port for withdrawing a bottoms stream from the quench column, (3) a top port for withdrawing an overhead stream from the quench column, (4) a quench port for introducing a quench stream into the quench column, where the quench port is located above the feed port, and (5) an upper port for introducing a liquid stream comprising overhead condensibles and a second portion of the bottoms stream to improve liquid-gas interactions within the quench column. The apparatus also includes a bottoms recycle system. The bottoms recycle stream includes: (1) a first splitter valve to divide the bottoms stream into a product stream and a recycle stream, and (2) a second splitter valve to divide the recycle stream into the quench stream and a top recycle stream. The apparatus also includes a top recycle system. The top recycle system includes: (1) at least one separator to separate the overhead stream into a vapor stream and an overhead liquid stream, and (2) a mixing valve to combine the liquid stream and the top recycle stream forming the liquid stream. The apparatus is operated so that a mass ratio of the first portion of the bottoms stream to the hot stream is at least 5:1, a mass ratio of the first portion of the bottoms stream to the second portion of the bottoms stream is at least 5:1, and a temperature of the quench stream is at or below about 75° C.

The present invention further provides a process for separating MAA and AA in a stripper/absorber system including the step of introducing a stream comprising MA, MAA and AA to an absorber column through a lower side port. Afterwards, a first absorbent stream is introduced into a top side port of the absorber column, and a second absorbent stream is introduced into an upper side port of the absorber column. An absorber bottoms stream is withdrawn from a bottom port of the absorber column, and a waste overhead stream withdrawing from a top port of the absorber column. The absorber bottoms stream is forwarded to a top input port of a stripper column, while a stripper gas stream is introduced into a lower side port of the stripper column. An overhead stream comprising substantially all of the MA is withdrawn from a top output port of the stripper column, and a stripper bottoms stream is withdrawn from a bottom port of the stripper column. A portion of the stripper bottoms stream is recycled through a reboiler to a bottom side port of the stripper column. A relatively small split stream is taken from the remaining liquid leaving the stripper bottom. The split stream is combined with the aqueous stream taken from the quench condensate recycle loop. The process is operated so that a mass ratio of the split stream to the remaining liquid leaving the stripper bottom is governed by:

$$Y = C_1 + C_2 * X$$

where $C_1$ and $C_2$ are constants, Y is a ratio of mass flow in the split stream to the remaining mass flow of the liquid from the bottom of the stripper column, and X is the remaining mass flow of the liquid from the bottom of the stripper column.

BRIEF DESCRIPTION OF THE DRAWINGS

The invention can be better understood with reference to the following detailed description together with the appended illustrative drawings in which like elements are numbered the same.

DETAILED DESCRIPTION OF THE INVENTION

Figure 1:
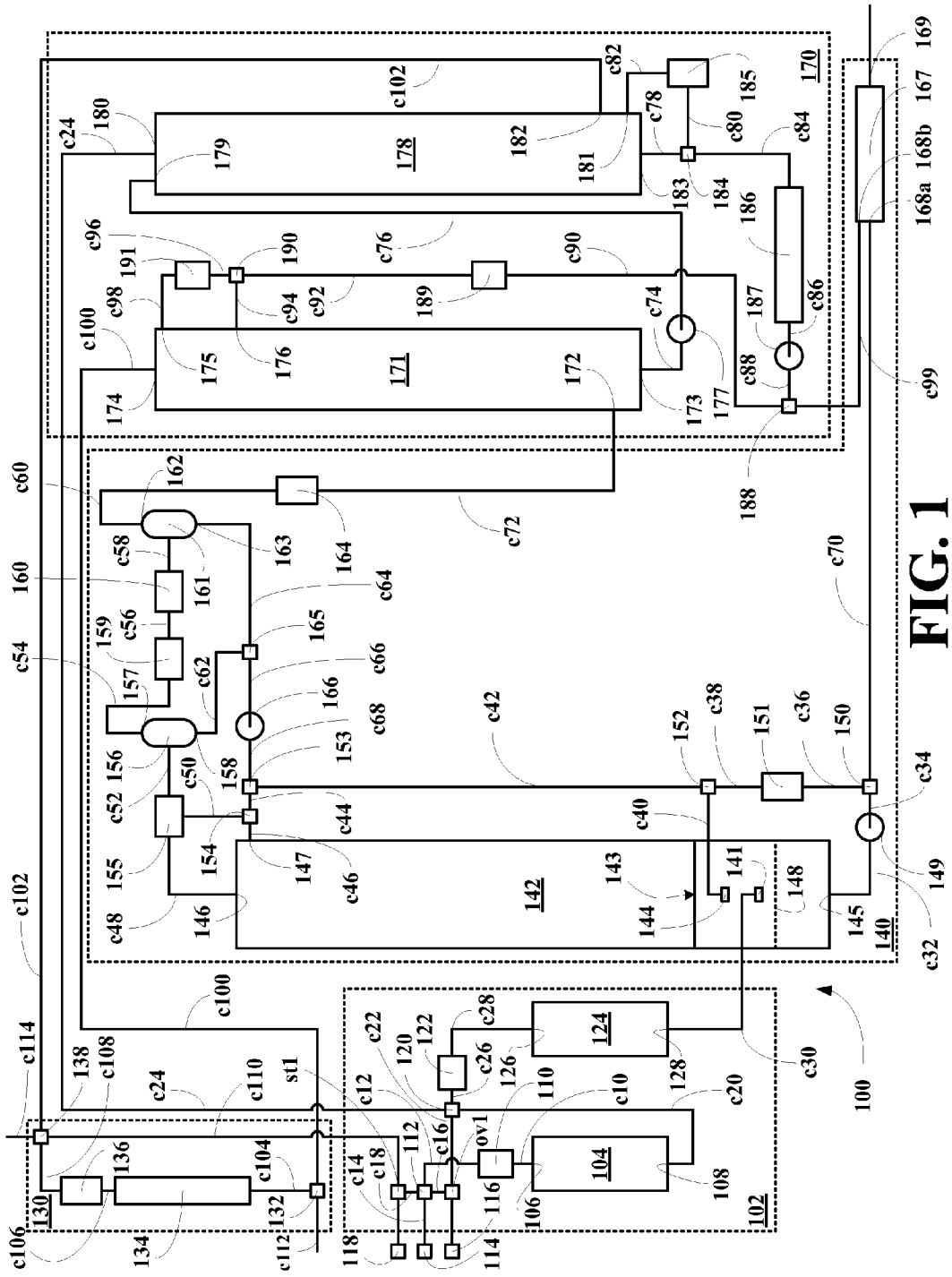
FIG. 1 depicts a schematic diagram of an embodiment of the process and system of this invention.

The inventors have found a system and process for separating methacrolein (MA) from methacrylic acid (MAA) and acetic acid (AA) in a gas phase product from partial oxidation of isobutene (IB) can be performed that maximizes the recovery of MA, MAA and AA at minimum capital and energy cost, under conditions that minimize polymerization and plugging by solids deposition in compressors, column, etc. The inventor has also found that the system and process can be adjusted to maximize process operation, improving MA recovery and conversion and reducing MAA losses.

This invention pertains to a system and process for separating methacrolein (MA) from methacrylic acid (MAA) and acetic acid in the gas phase product from partial oxidation of isobutylene (IB) in two oxidation steps. The objective is to maximize recovery of all three at minimum capital and energy cost, under conditions that minimize polymerization conditions and plugging by solids deposition in compressors, columns, etc. Another objective is to maximize process operability. These objectives are met by the following key characteristics of this system and process.

1. The initial quench of hot reaction gas from the second oxidation step is accomplished in 2-3 seconds by recycled condensate in a sump section of a quench column amounting to a near or substantially instantaneous quench of the hot reactor gas due to an overwhelming flood of recycled condensate in the sump section of the quench column. This rapid, near or substantially instantaneous, cooling minimizes by-product and polymerization reactions that occur when the gas is more gradually cooled. The entering gas temperature from the second oxidation reactor is about 280° C. and the condensate temperature is less than 70° C., and in certain embodiments about 67° C. To accomplish this near or substantially instantaneous quenching of the hot gases from the oxidation subsystem, a ratio of mass of recycled condensate to a mass of entering hot gas is about 7:1, and ratio of mass of recycled condensate to a mass of condensibles in the hot gas is about 70:1, where condensibles refers to that part of the hot gases that will condense under the quench column conditions. These conditions take advantage of the minimum boiling azeotrope for water and MA, which preferentially keeps MA in the gas phase in relation to MAA and acetic acid. Less than 0.1% of the unreacted MA from the second oxidation leaves in the liquid stream or bottoms stream, which is split from the recycled condensate and sent to MAA/acetic acid recovery. Thus, there is no need for costly recovery and recycle of unreacted MA back to the second oxidation step from this stream.

2. The non-condensed reaction gases leave the sump section of the quench column into the bottom of the quench column. A portion of the recycled condensate is cooled to about 55° C. using cooling water and enters the top of the quench column. A ratio of a mass flow of the cooled recycled condensate fed to top of the quench column to a mass flow of the recycle stream fed to the sump section of the quench is about 1:5. In certain embodiments, this mass ratio is about 1:5.5, and in other embodiments, the ratio is about 1:6. Because so much condensation takes place in the sump, there is reduced vapor and liquid traffic in the quench column above the sump. This allows a much smaller quench column diameter compared to having all of the recycled condensate fed to the top.

3. The vapor leaving the top of the quench column passes through a venturi scrubber to capture any fine particulates, formed from high boiling by-products in the oxidation reactors, into the liquid phase that were not captured in the sump and quench column. Enough liquid from the re-circulating condensate is diverted to the scrubber to make the volume ratio of gas to liquid entering the scrubber to be about 1000 to 1. This greatly reduces fouling and plugging problems in the downstream equipment.

4. The gas leaving the scrubber is separated from the liquid, compressed to about 10 psia and cooled to about 95° C. to partially condense it. It passes through another gas/liquid separator. The liquid is recycled back to the quench column and scrubber. These conditions of temperature and pressure are again controlled to take advantage of the minimum boiling azeotropic temperature of the MA/water binary. Thus, the gas leaving the quench area to the absorber/stripper system contains over 99.9% of the unreacted MA from the second oxidation reactor. It also contains about 43% of the acetic acid and about 9% of the MAA. This stream is intentionally passed to the absorber/stripper system. By controlling the recirculation rates, temperature and pressure of condensate around the quench column and scrubber, MA solubility in the recirculating liquid between the absorber and stripper columns is increased, thereby decreasing the required size of these columns.

5. The gas leaving the quench area is compressed from about 5 psia to about 49 psia before entering the absorber/stripper system. It is advantageous to compress the gas at this point, because it further reduces the required size of the absorber column; it provides pressure for ultimate recycle of inerts back to the first oxidation reactor and to the stripper column if needed; and it provides pressure for recycle of a MA stream back to the second oxidation reactor.

6. Recycled condensate used as the absorbent, enters the absorber column at two places or port. At a top side port of the absorber, a first portion of the absorbent feed stream is cooled to about 16° C. before entering the top port. At an upper side port located about 20% of the way down the absorber column, a second portion of the absorbent feed stream is cooled to about 21° C. before entering the upper port. A mass flow ratio of the first portion of absorbent feed to the second portion of the absorbent stream is about 1:5. In certain embodiments, this mass ratio is about 1:5.5, and in other embodiments, this mass ratio is about 1:57. This reduces the refrigeration load, while keeping product and by-product losses out the top of the absorber, as a percent of those components leaving the second oxidation reactor, to ~nil for MA, to ~1.1% for acetic acid, and to ~0.2% for MAA.

7. A bottoms stream from the absorber column is forwarded to a top input port of a stripper column. Conditions in the stripper column are controlled so that the temperature at the bottom of the stripper column does not exceed about 118° C. to minimize polymerization and to ensure that essentially zero MA leaves in a stripper column bottoms stream, and less than 0.1% of both acetic acid and methacrylic acid leave through a top output port of the stripper column. This can be achieved by controlling a pressure at a top portion of the stripper column to a value of about 25 psia, and then varying a bottom liquid rate by controlling heat (e.g., steam) supplied to a reboiler. A relatively small split stream, containing acetic acid and MAA among other components, is taken from the liquid leaving the stripper bottom. It has been found that a split fraction assigned to this stream should be controlled to vary in a direct linear manner to the bottom liquid flow rate in order to maintain stable column operation. The split stream is combined with the aqueous stream taken from the quench condensate recycle loop. The combined streams are sent for recovery of MAA and acetic acid products.

One method for operating the absorber/stripper subsystem is according to the following relationship:

$$Y=C_1+C_2*X$$

where $C_1$ and $C_2$ are constants, Y is a ratio of mass flow in the split stream to the mass flow of the remaining liquid from the bottom of the stripper column, and X is the remaining mass flow of the liquid from the bottom of the stripper column. These two variables, X and Y, cannot be varied independently without causing the process to go unstable. In certain embodiments, the constant $C_1$ has a value between about −0.035 and about −0.055, while the constant $C_2$ has a value between about 0.05 and about 0.07. In certain embodiments, the constant $C_1$ has a value between about −0.04 and about −0.05, while the constant $C_2$ has a value between about 0.055 and about 0.065. In other embodiments, $C_1$ has a value of about −0.0431 and $C_2$ has a value of about 0.0596.

Overall recovery of both MAA and acetic acid is about 99.5% based on the given selectivities to these products in the oxidation reactions, assuming reaction to extinction of perfectly recycled MA. This is believed to be a superior recovery for both products compared to any other processing method that has been disclosed for recovery of these products from a two step oxidation of isobutylene or tertiary butyl alcohol.

First System Embodiment

Referring now to FIG. 1, a system for producing methacrylic acid (MAA), generally 100, is shown to include an oxidation subsystem 102, a stripper gas subsystem 130, a quench/distillation subsystem 140, and an absorber/stripper subsystem 170.

Oxidation Subsystem

The oxidation subsystem 102 includes a first oxidation reactor 104 having a first inlet 106 and a first outlet 108. The first inlet 106 is connected to a first heat exchanger 110 via appropriate piping c10, which is in turn connected to a first mixing valve 112 via appropriate piping c12. The first mixing valve 112 is connected to an isobutene (IB) feed 114, an oxidizing agent feed 116, and a steam feed 118 and a recycle inert diluents gas stream 119 via appropriate piping c14, c16 and c18, respectively. The oxidizing agent feed 116 is actually connected to an oxidizing agent dividing valve ov1 and the steam feed 118 is actually connected to a steam mixing valve st1 by appropriate piping not labeled. The inert diluents gas stream c110 is also connected to the steam mixing valve st1.

The oxidation subsystem 102 also includes a second mixing valve 120 connected to the first outlet 108 via appropriate piping c20, to the oxidizing agent dividing value ov1 via appropriate piping c22 and to a top port 180 of a stripper column 178 (as described herein) via appropriate piping c24. The second mixing valve 120 is optionally connected to a second heat exchanger 122 via appropriate piping c26, which is in turn connect to a second oxidation reactor 124 at a second inlet 126 via appropriate piping c28. The second oxidation reactor 124 also includes a second outlet 128. The first and second reactors 104 and 124 are generally multiple tube reactors filled with a catalyst or having one or more catalyst zones in the tubes and cooled by a heat transfer fluid circulated about the tubes. The first reactor 104 generally includes a mixed metal oxide catalyst well known in the art for oxidizing IB to a methacrolein. Non-limiting and exemplary examples of suitable mixed metal oxide catalysts are disclosed in the following U.S. Pat. Nos. 3,907,712, 3,928,462, 3,929,899, 3,933,751, 3,936,505, 3,956,378, 4,012,449, 4,025,565, 4,035,418, 4,111,984, 4,170,570, 4,171,454, 4,190,608, 4,224,193, 4,240,931, 4,250,339, 4,252,683, 4,258,217, 4,261,858, 4,267,385, 4,267,386, 4,271,040, 4,272,408, 4,292,203, 4,306,088, 4,306,090, 4,332,971, 4,339,355, 4,354,044, 4,377,501, 4,380,664, 4,404,397, 4,413,147, 4,414,134, 4,424,141, 4,446,328, 4,454,346, 4,489,170, 4,503,247, 4,511,671, 4,535,188, 4,537,874, 4,547,588, 4,556,731, 4,558,029, 4,596,784, 4,732,884, 4,778,930, 4,803,190, 4,816,603, 4,871,700, 4,916,103, 4,925,823, 4,946,819, 4,954,650, 5,059,573, 5,072,052, 5,081,314, 5,082,819, 5,094,990, 5,102,847, 5,132,269, 5,138,100, 5,144,090, 5,155,262, 5,166,119, 5,183,936, 5,198,578, 5,221,653, 5,225,389, 5,245,083, 5,250,485, 5,264,627, 5,276,178, 5,300,707, 5,349,092, 5,364,825, 5,380,933, 5,491,258, 5,532,199, 5,602,280, 5,670,702, 5,684,188, 5,728,894, 5,739,391, 5,817,865, 5,821,390, 5,856,259, 6,028,220, 6,069,271, 6,171,571, and RE32,082, incorporated herein by reference. The second reactor 124 generally includes a heteropolyacid catalyst well known in the art for oxidizing methacrolein to methacrylic acid. Non-limiting and exemplary examples of suitable heteropolyacid catalysts are disclosed in the following U.S. Pat. and application Ser. Nos. 3,840,595, 3,865,873, 3,875,220, Re 29,901, 3,925,464, 3,954,856, 3,956,182, 3,959,384, 3,965,163, 3,968,165, 3,968,166, 3,972,920, 3,978,003, 3,998,876, 3,998,877, 4,000,088, 4,001,316, 4,017,423, 4,035,418, 4,042,533, 4,042,625, 4,051,179, 4,052,450, 4,070,397, 4,101,448, 4,115,441, 4,118,419, 4,124,634, 4,138,366, 4,165,296, 4,166,190, 4,169,070, 4,172,051, 4,180,678, 4,212,767, 4,223,161, 4,255,466, 4,238,359, 4,240,930, 4,250,054, 4,252,681, 4,252,682, 4,252,683, 4,259,211, 4,261,858, 4,261,859, 4,261,860, 4,271,040, 4,272,408, 4,273,676, 4,297,247, 4,301,030, 4,301,031, 4,305,843, 4,314,074, 4,319,042, 4,320,227, 4,339,355, 4,341,900, 4,347,163, 4,356,316, 4,358,608, 4,358,610, 4,364,844, 4,374,757, 4,377,501, 4,404,397, 4,409,128, 4,415,752, 4,419,270, 4,424,141, 4,440,948, 4,443,555, 4,444,906, 4,444,907, 4,454,346, 4,467,113, 4,469,810, 4,471,061, 4,471,062, 4,489,170, 4,503,247, 4,521,618, 4,528,398, 4,530,916, 4,536,483, 4,547,588, 4,558,028, 4,558,029, 4,564,607, 4,565,801, 4,595,778, 4,621,155, 4,652,673, 4,720,575, 4,745,217, 4,757,038, 4,803,302, 4,804,778, 4,814,305, 4,816,603, 4,891,347, 4,925,823, 4,925,980, 4,954,650, 4,966,990, 4,968,838, 4,985,592, 5,093,521, 5,102,846, 5,102,847, 5,104,844, 5,126,307, 5,153,162, 5,173,468, 5,198,579, 5,206,431, 5,221,767, 5,239,115, 5,264,627, 5,420,091, 5,422,326, 5,521,137, 5,550,095, 5,569,636, 5,618,974, 5,981,804, 5,990,348, 6,043,184, 6,060,419, 6,169,202, 11/189,095, 11/189,116 and 11/189,126, incorporated herein by reference.

Quench/Distillation Subsystem

The second outlet 128 is connected to the quench/distillation subsystem 140 at a feed inlet 141 of a quench column 142 via appropriate piping c30. Typically, piping c30 would include jacketing along the length just outside the wall of 142 to, and including, downward directed inlet 141. A small amount of essentially inert gas fed to the jacketed side surrounds the main product from the second reactor 124 as it enters the quench at the feed inlet 141 to minimize plugging of the feed inlet 141 by solid deposition due to premature cooling. This inert gas could be a slip stream (not shown) from either c100, or low pressure steam from the feed stream 118, for example. The feed inlet 141 is located in a sump zone 143 of the quench column 142. The quench column 142 also includes a recycle inlet 144 located above the feed inlet 141, a bottoms outlet 145, an overhead outlet 146, and an upper inlet 147. The feed inlet 141 is generally located above a liquid level 148 in the sump zone 143.

The quench/distillation subsystem 140 also includes a first pump 149 connected to the bottoms outlet 145 appropriate piping c32. The pump 149 is in turn connect to a first dividing valve 150 via appropriate piping c34 and to a third heat exchanger 151 via appropriate piping c36. The third heat exchanger 151 is connected to a second dividing valve 152 via appropriate piping c38. The second dividing valve 152 is connected to the recycle inlet 144 via appropriate piping c40 and to a third mixing valve 153 via appropriate piping c42. The third mixing valve 153 is connected to a third dividing valve 154 via appropriate piping c44. The third dividing valve 154 is connected to the upper inlet 147 via appropriate piping c46.

The overhead outlet 146 is connected to a venturi valve 155 via appropriate piping c48. The venturi valve 155 is also connected to the third dividing valve 154 via appropriate piping c50 and to a first separator 156 via appropriate piping c52. The first separator 156 includes a first vapor outlet 157 and a first liquid outlet 158. The first vapor outlet 157 is connected to a first compressor 159 via appropriate piping c54. The first compressor 159 is connected to a fourth heat exchanger 160 via appropriate piping c56. The fourth heat exchanger 160 is connected to a second separator 161 via appropriate piping c58. The fourth heat exchanger 160 can be a single heat exchanger or two heat exchangers in series, where the first is water cooled and the second is cooled by refrigerant, thus not requiring the total cooling load to be borne by expensive refrigeration. The second separator 161 includes a second vapor outlet 162 and a second liquid outlet 163. The second vapor outlet 162 is connected to a second compressor 164 via appropriate piping c60.

The first liquid outlet 158 of the first separator 156 and the second liquid outlet 163 of the second separator 161 are connected a fourth mixing valve 165 via appropriate piping c62 and c64, respectively. The fourth mixing valve 165 is connected to a second pump 166 via appropriate piping c66, which is in turn connected to the third mixing valve 153 via appropriate piping c68, completing the quench/distillation subsystem 140.

The quench/distillation subsystem 140 also includes a first surge tank 167 connected to the first dividing valve 150 via appropriate piping c70, which includes a first inlet 168a, a second inlet 168b and an outlet 169.

Absorber/Stripper Subsystem

The absorber/stripper subsystem 170 includes an absorber column 171. The absorber column 171 includes a lower feed inlet 172 connected to the second compressor 164 via appropriate piping c3. The absorber 171 includes a bottoms outlet 173, an overhead outlet 174, a top inlet 175 and an upper inlet 176. The bottoms outlet 173 is connected to a third pump 177 via appropriate piping c5, which is in turn connected to a stripper column 178 at a top feed inlet 179 via appropriate piping c7. The stripper column 178 also includes an overhead outlet 180, a recycle lower inlet 181, a stripper gas inlet 182 and a bottoms outlet 183. The stripper column 178 also includes a fourth dividing valve 184 and a re-boiler 185. The fourth dividing valve 184 is connected to the bottoms outlet 183 and the re-boiler 185 via appropriate piping c9 and c11, respectively. The re-boiler 185 is also connected to the recycle lower inlet 181 via appropriate piping c13. The fourth dividing valve 184 is also connected to a second surge tank 186 via appropriate piping c15. The surge tank 186 is connected to a fourth pump 187 via appropriate piping c17, which is in turn connected to a fifth dividing valve 188 via appropriate piping c19. The fifth dividing valve 188 is connected to a fifth heat exchanger 189 via appropriate piping c21, which is in turn connected to a sixth dividing valve 190 via appropriate piping c23. The sixth dividing valve 190 is connected to the upper inlet 176 via appropriate piping c25 and to a sixth heat exchanger 191 via appropriate piping c27. The sixth heat exchanger 191 is connected to the top inlet 175 via appropriate piping c29. The fifth dividing valve 188 is also connected to the second inlet 168b of the first surge tank via appropriate piping c99.

The overhead outlet 180 of the stripper column 178 is connected to second mixing valve 120 via the piping c24. The overhead 174 of the absorber column 171 is connected to the stripper gas subsystem 130 at a fifth mixing valve 132 via appropriate piping c31. The stripper gas inlet 182 of the stripper column 178 is connected to a sixth dividing valve 138 of the stripper gas subsystem 130 via appropriate piping c33.

Stripper Gas Subsystem

The stripper gas subsystem 130 includes the fifth mixing valve 132 which is connected to an incinerator 134 via appropriate piping c104 and optionally to piping c112 which forwards a stream to be incinerated to the incinerator 134. The incinerator 134 is connected to a seventh heat exchanger 136 via appropriate piping c106, which is in turn connected to the sixth dividing valve 138 via appropriate piping c108. The sixth dividing valve 138 is connected to the steam mixing valve st1 via appropriate piping c110 and to the stripper gas inlet 182 of the stripper column 178 via the piping c102. The sixth dividing valve 138 can also be connected to a piping c114 supporting a vent stream.

Operation of First System Embodiment

Figure 2A:
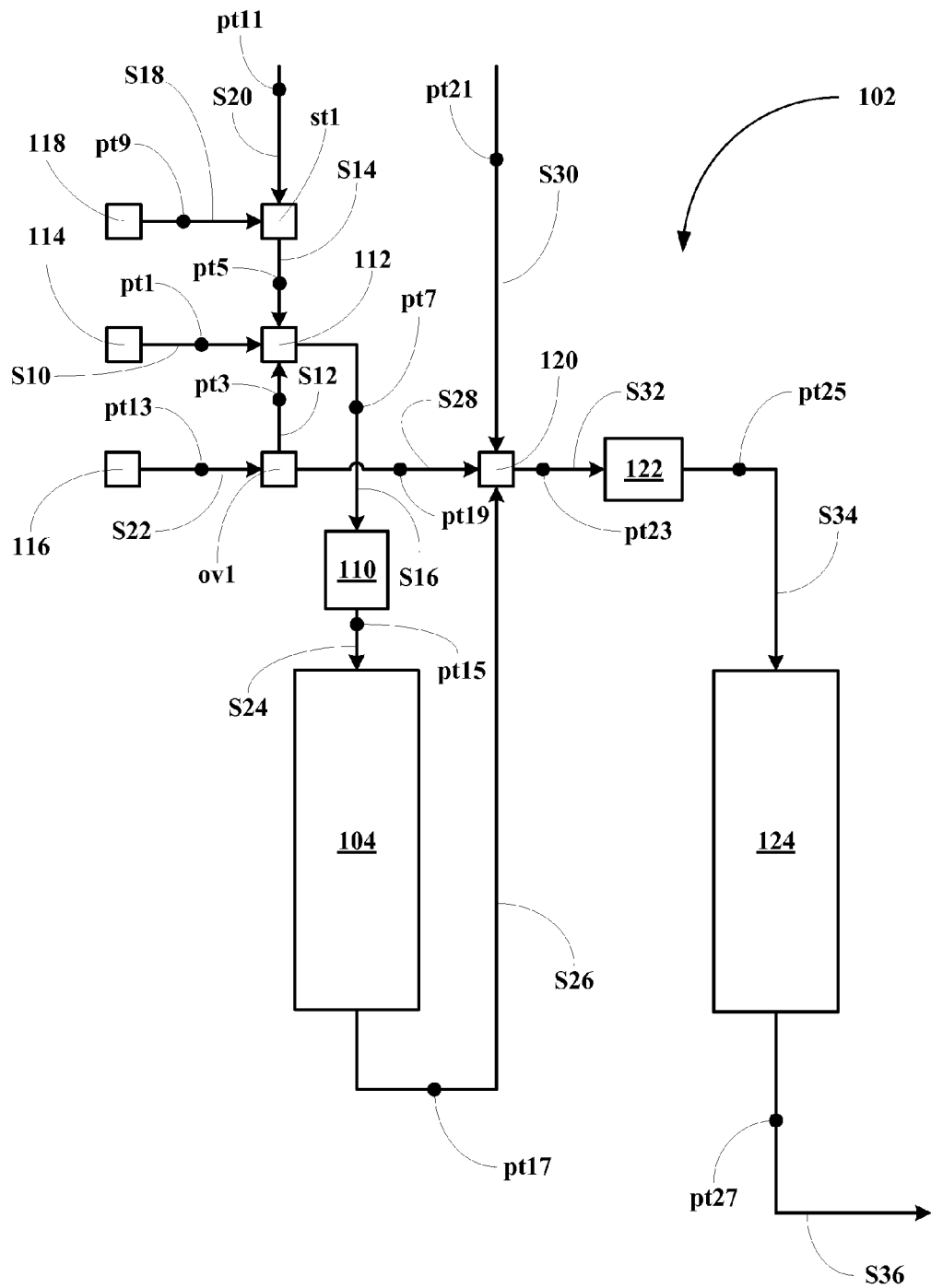
FIG. 2A depicts an expanded schematic diagram of the oxidation subsystem of FIG. 1.
Figure 2B:
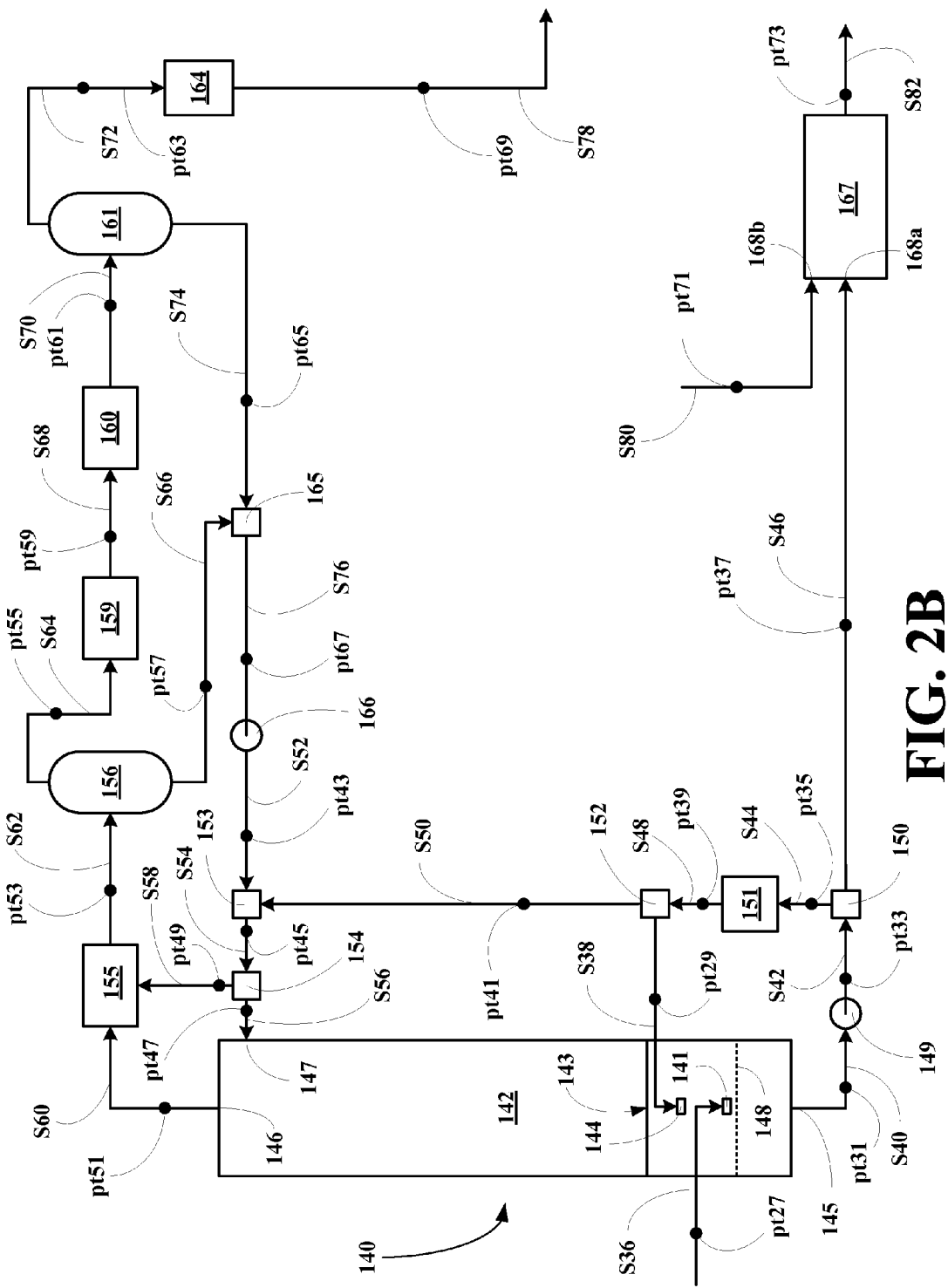
FIG. 2B depicts an expanded schematic diagram of the quench/distillation subsystem of FIG. 1.
Figure 2C:
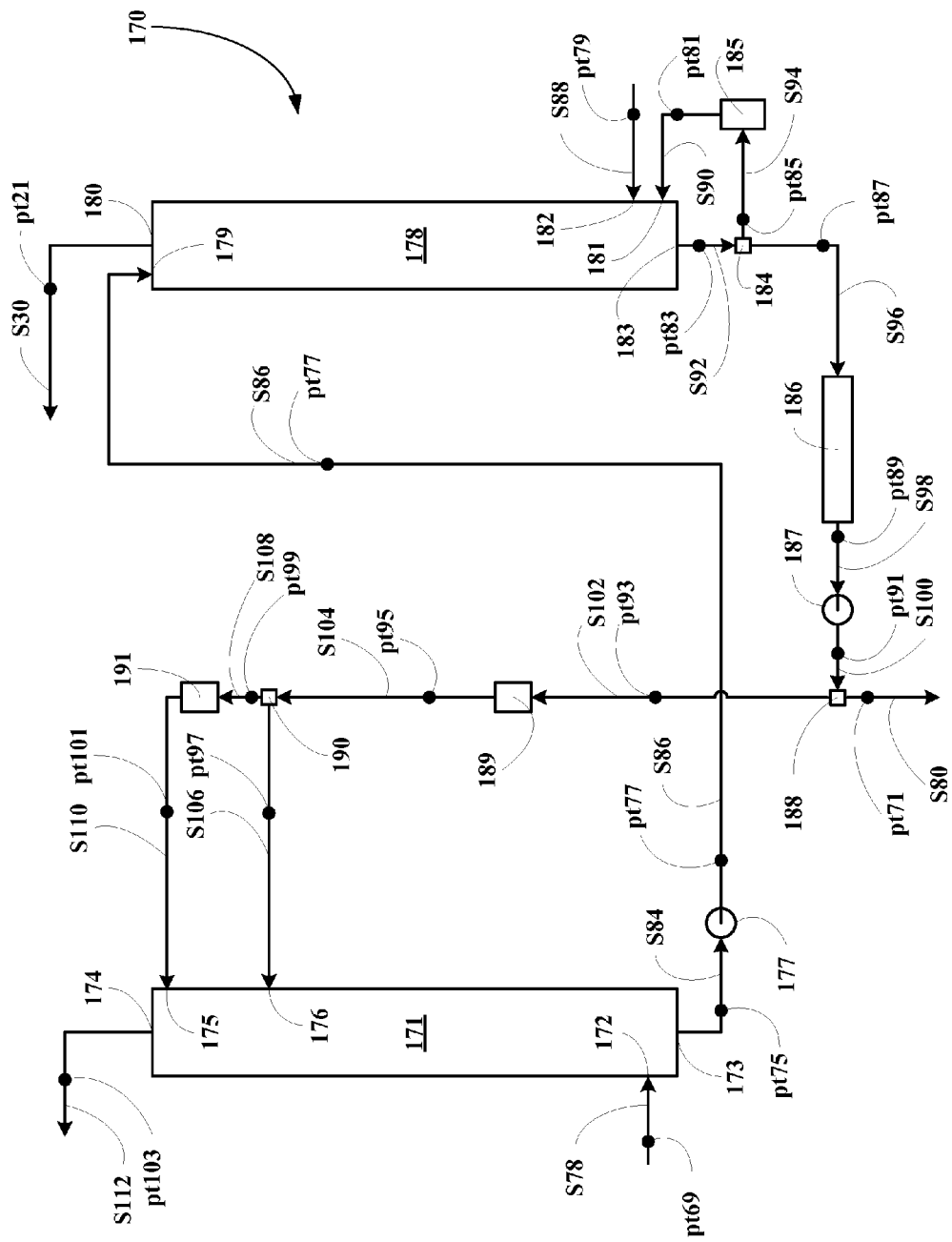
FIG. 2C depicts an expanded schematic diagram of the absorber/stripper subsystem of FIG. 1.
Figure 2D:
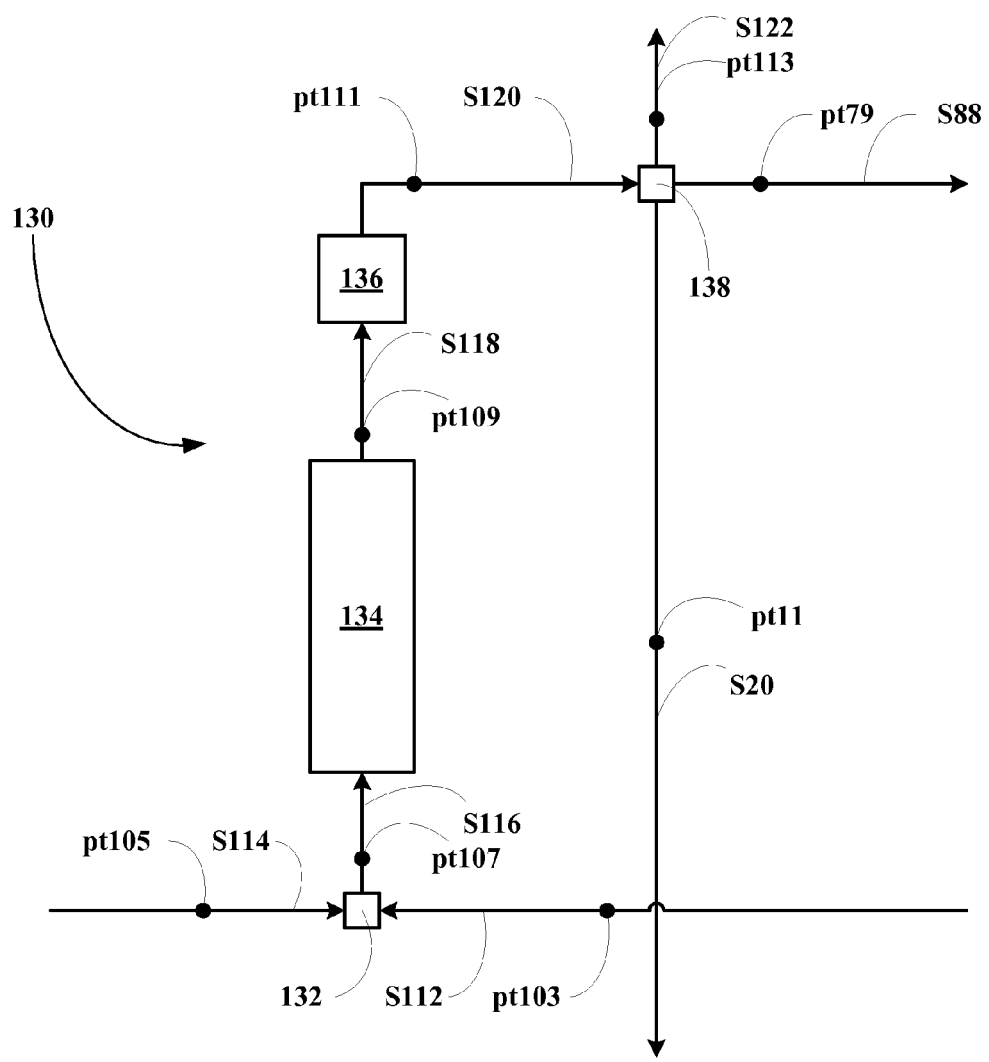
FIG. 2D depicts an expanded schematic diagram of the stripper gas subsystem of FIG. 1.

Referring now to FIGS. 2A-D, four expanded views of the system of the FIG. 1 are set forth, where the figures describe the operation of the four components of the system of FIG. 1: the Oxidation Subsystem, FIG. 2A, the Quench/distillation Subsystem, FIG. 2B, the Absorber/stripper Subsystem, FIG. 2C, and the Stripper Gas Subsystem, FIG. 2D.

Oxidation Subsystem

Referring now to FIG. 2A, the expanded view of the oxidation subsystem 102 of FIG. 1 is shown and its operation described in terms of streams. The properties or parameters of each stream are associated with a point, where the properties and parameters of the stream include physical and/or chemical parameters such as composition, pressure, temperature, state (liquid, mixed, vapor, etc.), or other relevant properties or parameters.

In the first mixing valve 112, an isobutene (IB) feed stream S10 having parameters as at a point pt1 supplied by an isobutene supply 114, a first oxidizing agent stream S12 having parameters as at a point pt3 and a mixed stream S14 having parameters as at a point pt5 are combined to form a first input stream S16 having parameters as at a point pt7. The mixed stream S14 having the parameters as at the point pt5 is derived from a mixing valve st1, which combines a steam stream S18 and an inert diluent recycle stream S20, having parameters as at points pt9 and pt11, respectively. The stream S18 having the parameters as at the point pt9 is supplied from the steam source 118; while the stream S20 having the parameters as at the point pt11 is supplied from the stripper gas subsystem 130. The oxidizing agent stream S12 having the parameters as at the point pt3 is derived from a dividing valve ov1, which is supported by an oxidizing agent feed stream S22 having parameters as at a point pt13, which comes from a oxidizing agent supply 116. Although the IB feed stream S10 and oxidizing agent stream S12 are at a moderately low temperature of about 85° F., upon mixing with the steam stream S18 and the diluent stream S20, the combined stream is significantly increased in temperature as set forth in Table I herein.

The first input stream S16 having the parameters as at the point pt7 then passes through the first heat exchanger 110, where it is heated to form a heated first input stream S24 having parameters as at a point pt15 in a first heat exchange step pt7-pt15. The heated first input stream S24 having the parameter as at the point pt15 is then forwarded to the first oxidation reactor 104 where it is partially oxidized over a mixed metal oxide catalyst (as described above) to from a methacrolein-containing stream S26 having parameters as at a point pt17. The methacrolein-containing stream S26 having the parameters as at the point pt17 is then forwarded to the second mixing valve 120, where it is combined with a second oxidizing agent stream S28 having parameters as at a point pt19 and a methacrolein recycle stream S30 having parameters as at a point pt21 to form a second input stream S32 having parameters as at a point pt23. The methacrolein recycle stream S30 having the parameters as at the point pt21 is derived from the absorber/stripper subsystem 170 (as described below).

The second input stream S32 having the parameters as at the point pt23 is then passed through the second heat exchanger 122, where it is heated to form a heated second input stream S34 having parameters as at a point pt25 in a second heat exchange step pt23-pt25. The heated second input stream S34 having the parameters as at the point pt25 is then forwarded to the second oxidation reactor 124, where it is partially oxidized over a heteropolyacid catalyst (as described above) to form a crude methacrylic acid stream S36 having parameters as at a point pt27.

Quench/Distillation Subsystem Operational Description

Referring now to FIG. 2B, the expanded view of the oxidation subsystem 140 of FIG. 1 is shown and its operation described in terms of streams and streams parameters as described above. The crude methacrylic acid stream S36 having the parameters as at the point pt27 is feed into the quench column 142 of the quench/distillation subsystem 140 through the inlet 141 as described above. The crude methacrylic acid stream S36 is rapidly cooled in the sump portion 143 of the quench column 142 by a first recycle substream S38 having parameters as at a point pt29, which is fed into the column 142 via the inlet 144, which is generally a downward directed spray apparatus. A flow rate of the first recycle stream S38 having the parameters as at the point pt29 is sufficiently greater than a flow rate of the methacrylic acid stream S36 having the parameters as at the point pt27 to instantaneously or near instantaneously cool the methacrylic acid stream S36 from a temperature above 250° C. to a temperature below about 70° C. This rapid, instantaneous or near instantaneous, cooling reduces polymerization and increases column efficiency. The term rapid and near instantaneous cooling means that the cooling takes place quickly enough to reduce the stream S36 from 250° C. to 70° C. in a matter of a few seconds, less than 30 seconds. In certain embodiments, the stream S36 is cooled in less than 15 seconds. In certain other embodiments, the stream S36 is cooled in less than 5 seconds.

At the bottoms outlet 145, an enriched methacrylic acid stream S40 having parameters as at a point pt31 is withdrawn from the column 142. The enriched methacrylic acid stream S40 having the parameters as at the point pt31 is then pumped to a higher pressure in the first pump 149 to form a higher pressure methacrylic acid stream S42 having parameters as at a point pt33. The higher pressure stream S42 having the parameters as at the point pt33 is then forwarded to the first dividing valve 150, where the stream S42 is divided into a recycle stream S44 having parameters as at a point pt35 and a methacrylic acid product stream S46 having parameters as at a point pt37. The recycle stream S44 is passed through the third heat exchanger 151 to form a cooled recycle stream S48 having parameters as at a point pt39. The cooled recycle stream S48 is then divided into the first recycle substream S38 having the parameters as at the point pt29 and a second recycle substream S50 having parameters as at a point pt41. The second recycle substream S50 is forwarded to the third mixing valve 153, where it is combined with a stream S52 having parameters as at a point pt43 to form a combined recycle stream S54 having parameters as at a point pt45. The combined recycle stream S54 is forwarded to the third dividing valve 154, where it is divided into a top recycle stream S56 having parameters as at a point pt47 and a venturi carrier stream S58 having parameters as at a point pt49.

The column 142 also produces an overhead stream S60 having parameters as at a point pt51, which exits the column 142 at the overhead outlet 146. The overhead stream S60 is forwarded to the venturi valve 155, where it is mixed with the venturi carrier stream S58. The venturi valve 155 is designed to remove fine particles from the overhead vapor stream S60 to produce a two-phased overhead stream S62 with essentially all fine particles contained in the liquid phase having parameters as at a point pt53. The cleaned overhead stream S62 is forwarded to the first separator 156, where it is separated into a first vapor stream S64 with essentially no particulates having parameters as at a point pt55 and a first liquid stream S66 having parameters as at a point pt57. The first vapor stream S64 is forwarded to the first compressor 159 to form a higher pressure stream S68 having parameters as at a point pt59. The higher pressure stream S68 is then passed through the fourth heat exchanger 160 (or two heat exchangers as described above) to form a cooled partially condensed stream S70 having parameters as at a point pt61, which is forwarded to the second separator 161. The partially condensed stream S70 is separated into a second vapor stream S72 having parameters as at a point pt63 and a second liquid stream S74 having parameters as at a point pt65.

The second liquid stream S74 is then forwarded to the fourth mixing valve 165, where it is mixed with the stream S66 to form a combined liquid stream S76 having parameters as at a point pt67. The stream S76 is then pressurized in the second pump 166 to form the higher pressure liquid stream S52 having the parameters as at the point pt43. The second vapor stream S72 having the parameters as at the point pt63 is then passed through the second compressor 164 to form a compressed stream S78 having parameters as at a point pt69.

The product methacrylic acid stream S46 having the parameters as at the point pt37 is forwarded to the first inlet 168a of the first surge tank 167. A second methacrylic acid product stream S80 having parameters as at a point pt71 coming from the absorption/stripper subsystem 170 enters the first surge tank 167 via the second inlet 168b. A combined methacrylic acid product stream S82 having parameters as at a point pt73 is then forwarded to methacrylic acid purification and utilization systems (not shown).

Absorber/Stripper Subsystem

Referring now to FIG. 1C, the expanded view of the absorber/stripper subsystem 170 of FIG. 1 is shown and its operation described in terms of streams and streams parameters as described above. The compressed stream S78 having the parameters as at the point pt69 is fed into the absorption column 171 at the inlet 172. An absorber bottom stream S35 having parameters as at a point pt3 is withdrawn from the bottoms outlet 173 of the absorber column 171 and forwarded to the third pump 177, where its pressure is increased to form a higher pressure bottoms stream S37 having parameters as at a point pt5. The stream S86 is then fed into the top inlet 179 of the stripper column 178. In the stripper column 178, the down flowing absorber bottoms in the stream S86 are mixed with an upcoming gas flow from a stripper gas stream S39 having parameters as at a point pt7 entering at the stripper gas inlet 182 and a reboiler stream S41 having parameters as at a point pt9 entering at the reboiler inlet 181 under conditions so that the stripper column 178 produces a bottoms stream S43 having parameters as at a point pt11 at the bottoms outlet 183 enriched in methacrylic acid and the overhead stream S30 having the parameters as at the point pt21 at the overhead outlet 180 enriched in methacrolein. The overhead stream S30 having the parameters as at the point pt21 is then mixed with the stream S28 having the parameters as at the point pt19 and the stream S26 having the parameter as at the point pt17 to form the stream S32 having the parameters as at the point p123, which after heating is oxidized in the second reactor 124 as described above.

The bottom stream S92 having the parameters as at the point pt83 is forwarded to the fourth dividing valve 184, where it is divided into a first bottoms substream S94 having parameters as at a point pt85 and a second bottoms substream S96 having parameters as at a point pt87. The first substream S94 is forwarded to the reboiler 185, where it is heated to form the stream S90 having the parameters as at the point pt81. The second substream S96 having the parameters as at the point pt87 is forwarded to the second surge tank 186. A methacrylic acid rich stream S98 having parameters as at a point pt89 is withdrawn from the second surge tank 186 and forwarded to the fourth pump 187 to form a higher pressure methacrylic acid rich stream S100 having parameters as at a point pt91. The stream S100 is then forwarded to the fifth dividing valve 188 to form the methacrylic acid rich stream S80 having parameters as at a point pt71 and a higher pressure methacrylic acid recycle stream S102 having parameters as at a point pt93. The stream S102 is forwarded to the fifth heat exchanger 189 to form a cooled stream S104 having parameters as at a point pt95. The cooled stream S104 is then divided via the sixth dividing valve 190 into an upper recycle stream S106 having parameters as at a point pt97, which is fed into the absorber column 171 at the upper inlet 176, and a cooled substream S108 having parameters as at a point pt99. The cooled substream S108 is further heated to form a top recycle stream S110 having parameters as at a point pt101, which is fed into the absorber column 171 at the top inlet 175. In the absorber column 171, the two methacrylic acid rich recycle stream S106 and S110 are used to absorb methacrolein in the stream S78 so that it can be separated in the stripper column and recycled to the second reactor, while an overhead stream S112 having parameters as at a point pt103 withdrawn from the overhead outlet 174 of the absorber column is sent to the incinerator 134 to form the stripper gas stream S88.

Stripper Gas Subsystem

Referring now to FIG. 2D, the expanded view of the stripper gas subsystem 130 of FIG. 1 is shown and its operation described in terms of streams and streams parameters as described above. The absorber overhead stream S112 having the parameters as at the point pt103, which is a waste lights stream, is fed into the mixing valve 132, where it can be mixed with an external waste stream S114 having parameters as at a point pt105 to form an incinerator stream S116 having parameters as at a point pt107. The incinerator stream S116, along with an oxygen stream (not shown) to supply oxygen as needed for combustion, is then passed through the incinerator 134 where it is burned to from a flue gas stream S118 having parameters as at a point pt109. The flue gas stream S118 is then forwarded to the sixth heat exchanger 136 to form a cooled flue gas stream S120 having parameters as at a point pt111. The cooled flue gas stream S120 is then forwarded to the sixth dividing valve 138, which produces the inert diluents recycle stream S20 having parameters as at the point pt11, the stripper gas stream S88 having the parameters as at the point pt79 and a purge stream S122 having parameters as at a point pt113.

The overall process can be further understood with reference to the following stream/parameter tables. Table I tabulates certain critical physical/chemical properties of the stream associated with the oxidation subsystem of the process flow diagrams of FIG. 2A-D. Table II tabulates certain critical physical/chemical properties of the stream associated with the quench distillation subsystem of the process flow diagrams of FIG. 2A-D. Table III tabulates certain critical physical/chemical properties of the stream associated with the absorber/stripper subsystem of the process flow diagrams of FIG. 2A-D. Table IV tabulates certain critical physical/chemical properties of the stream associated with the stripper gas subsystem of the process flow diagrams of FIG. 2A-D.

TABLE I

Stream Properties in Oxidation Subsystem

| Parameters | S10 | S12 | S16 | S18 | S20 | S24 |
|---|---|---|---|---|---|---|
| Temperature ° C. | 29.44 | 29.44 | 183.1 | 162.39 | 259.78 | 225.00 |
| (° F.) | (85.00) | (85.00) | (361.60) | (324.30) | (499.60) | (437.00) |
| Pressure psi | 65.00 | 100.00 | 34.00 | 95.00 | 34.00 | 32.00 |
| Vapor Frac | 0.000 | 1.000 | 1.000 | 1.000 | 1.000 | 1.000 |
| Mole Flow lbmol/hr | 504.23 | 606.21 | 8415.22 | 711.51 | 6593.27 | 8415.22 |
| Mass Flow lb/hr | 28291.20 | 19397.91 | 341420.85 | 12818.00 | 280913.74 | 341420.85 |
| Volume Flow cuft/hr | 778.33 | 35264.27 | 2173790.00 | 61044.98 | 1992950.00 | 2524290.00 |
| Enthalpy MMBtu/hr | −8.07 | 0.02 | −1077.90 | −72.63 | −997.23 | −1070.86 |
| Mass Flow lb/hr | | | | | | |
| $N_2$ | 0.00 | 0.00 | 0.00 | 0.00 | 0.00 | 0.00 |
| CO | 0.00 | 0.00 | 0.00 | 0.00 | 0.00 | 0.00 |
| $O_2$ | 0.00 | 19397.91 | 35012.55 | 0.00 | 15614.64 | 35012.55 |
| $CO_2$ | 0.00 | 0.00 | 262947.01 | 0.00 | 262947.01 | 262947.01 |
| DME | 0.00 | 0.00 | 0.00 | 0.00 | 0.00 | 0.00 |
| Isobutene | 28291.20 | 0.00 | 28291.20 | 0.00 | 0.00 | 28291.20 |
| Acetaldehyde | 0.00 | 0.00 | 0.00 | 0.00 | 0.00 | 0.00 |
| Acrolein | 0.00 | 0.00 | 0.00 | 0.00 | 0.00 | 0.00 |
| Acetone | 0.00 | 0.00 | 0.00 | 0.00 | 0.00 | 0.00 |
| Methanol | 0.00 | 0.00 | 0.00 | 0.00 | 0.00 | 0.00 |
| MA | 0.00 | 0.00 | 0.00 | 0.00 | 0.00 | 0.00 |
| Water | 0.00 | 0.00 | 15170.08 | 12818.00 | 2352.08 | 15170.08 |
| MMA | 0.00 | 0.00 | 0.00 | 0.00 | 0.00 | 0.00 |
| MNPK | 0.00 | 0.00 | 0.00 | 0.00 | 0.00 | 0.00 |
| Toluene | 0.00 | 0.00 | 0.00 | 0.00 | 0.00 | 0.00 |
| Acetic acid | 0.00 | 0.00 | 0.00 | 0.00 | 0.00 | 0.00 |
| AA | 0.00 | 0.00 | 0.00 | 0.00 | 0.00 | 0.00 |
| MAA | 0.00 | 0.00 | 0.00 | 0.00 | 0.00 | 0.00 |
| Heavy Ends | 0.00 | 0.00 | 0.00 | 0.00 | 0.00 | 0.00 |
| $H_2SO_4$ | 0.00 | 0.00 | 0.00 | 0.00 | 0.00 | 0.00 |
| Heavy Organics | 0.00 | 0.00 | 0.00 | 0.00 | 0.00 | 0.00 |
| N-butane | 0.00 | 0.00 | 0.00 | 0.00 | 0.00 | 0.00 |
| Formaldehyde | 0.00 | 0.00 | 0.01 | 0.00 | 0.01 | 0.01 |
| Ethyl acetate | 0.00 | 0.00 | 0.00 | 0.00 | 0.00 | 0.00 |
| N-hexane | 0.00 | 0.00 | 0.00 | 0.00 | 0.00 | 0.00 |

| Parameters | S26 | S28 | S30 | S32 | S34 | S36 |
|---|---|---|---|---|---|---|
| Temperature ° C. | 390.00 | 29.44 | 71.06 | 364.94 | 225.00 | 280.00 |
| (° F.) | (734.00) | (85.00) | (159.90) | (688.90) | (437.00) | (536.00) |
| Pressure psi | 22.00 | 100.00 | 25.00 | 22.00 | 20.00 | 10.00 |
| Vapor Frac | 1.000 | 1.000 | 0.997 | 1.000 | 1.000 | 1.000 |
| Mole Flow lbmol/hr | 8486.32 | 561.57 | 261.39 | 9309.27 | 9309.27 | 9259.68 |
| Mass Flow lb/hr | 341420.85 | 17969.43 | 11939.87 | 371330.14 | 371330.14 | 371330.14 |
| Volume Flow cuft/hr | 4937240.00 | 32667.37 | 68195.59 | 5210890.00 | 4470270.00 | 9886360.00 |
| Enthalpy MMBtu/hr | −1171.07 | 0.02 | −31.31 | −1202.36 | −1229.59 | −1309.94 |
| Mass Flow lb/hr | | | | | | |
| $N_2$ | 0.00 | 0.00 | 0.00 | 0.00 | 0.00 | 0.00 |
| CO | 1807.84 | 0.00 | 3.34 | 1811.18 | 1811.18 | 5161.99 |
| $O_2$ | 9089.28 | 17969.43 | 10.64 | 27069.34 | 27069.34 | 11962.04 |
| $CO_2$ | 271490.60 | 0.00 | 5494.00 | 276984.60 | 276984.60 | 283961.96 |
| DME | 0.00 | 0.00 | 0.00 | 0.00 | 0.00 | 0.00 |
| Isobutene | 452.66 | 0.00 | 0.00 | 452.66 | 452.66 | 0.00 |
| Acetaldehyde | 488.69 | 0.00 | 117.99 | 606.68 | 606.68 | 121.34 |
| Acrolein | 141.35 | 0.00 | 914.01 | 1055.36 | 1055.36 | 939.14 |
| Acetone | 527.15 | 0.00 | 1451.31 | 1978.45 | 1978.45 | 1582.76 |
| Methanol | 0.00 | 0.00 | 0.00 | 0.00 | 0.00 | 0.00 |
| MA | 26683.31 | 0.00 | 2963.40 | 29646.71 | 29646.71 | 2994.32 |
| Water | 27033.62 | 0.00 | 870.27 | 27903.89 | 27903.89 | 31606.88 |
| MMA | 0.00 | 0.00 | 0.00 | 0.00 | 0.00 | 0.00 |
| MNPK | 0.00 | 0.00 | 0.00 | 0.00 | 0.00 | 0.00 |
| Toluene | 0.00 | 0.00 | 0.00 | 0.00 | 0.00 | 0.00 |
| Acetic acid | 1877.39 | 0.00 | 42.16 | 1919.55 | 1919.55 | 4612.02 |
| AA | 72.67 | 0.00 | 0.05 | 72.73 | 72.73 | 316.57 |
| MAA | 1345.70 | 0.00 | 72.70 | 1418.40 | 1418.40 | 27789.80 |
| Heavy ends | 168.35 | 0.00 | 0.00 | 168.35 | 168.35 | 281.32 |
| $H_2SO_4$ | 0.00 | 0.00 | 0.00 | 0.00 | 0.00 | 0.00 |
| Heavy organics | 0.00 | 0.00 | 0.00 | 0.00 | 0.00 | 0.00 |
| N-butane | 0.00 | 0.00 | 0.00 | 0.00 | 0.00 | 0.00 |

TABLE I-continued

Stream Properties in Oxidation Subsystem

| | | | | | | |
|---|---|---|---|---|---|---|
| Formaldehyde | 242.25 | 0.00 | 0.00 | 242.25 | 242.25 | 0.00 |
| Ethyl acetate | 0.00 | 0.00 | 0.00 | 0.00 | 0.00 | 0.00 |
| N-hexane | 0.00 | 0.00 | 0.00 | 0.00 | 0.00 | 0.00 |

TABLE II

Stream Properties in Quench Distillation Subsystem

| Parameters | S38 | S40 | S42 | S44 | S46 | S48 |
|---|---|---|---|---|---|---|
| Temperature °C. | 67.00 | 66.94 | 66.94 | 67.00 | 66.94 | 67.00 |
| (°F.) | (152.60) | (152.50) | (152.50) | (152.60) | (152.50) | (152.60) |
| Pressure psi | 21.00 | 10.00 | 10.00 | 25.00 | 10.00 | 21.00 |
| Vapor Frac | 0.000 | 0.000 | 0.000 | 0.000 | 0.000 | 0.000 |
| Mole Flow lbmol/hr | 62167.19 | 72057.12 | 71048.32 | 71048.32 | 1008.80 | 71048.22 |
| Mass Flow lb/hr | 2501740.00 | 2899730.00 | 2859140.00 | 2859140.00 | 40596.27 | 2859140.00 |
| Volume Flow cuft/hr | 42208.44 | 48921.52 | 48236.62 | 48237.79 | 684.90 | 48238.20 |
| Enthalpy MMBtu/hr | −8738.93 | −10129.33 | −9987.52 | −9987.36 | −141.81 | −9987.35 |
| Mass Flow lb/hr | | | | | | |
| $N_2$ | 0.00 | 0.00 | 0.00 | 0.00 | 0.00 | 0.00 |
| CO | 0.70 | 0.81 | 0.80 | 0.80 | 0.01 | 0.80 |
| $O_2$ | 2.05 | 2.38 | 2.34 | 2.34 | 0.03 | 2.34 |
| $CO_2$ | 801.01 | 928.45 | 915.45 | 915.45 | 13.00 | 915.44 |
| DME | 0.00 | 0.00 | 0.00 | 0.00 | 0.00 | 0.00 |
| Isobutene | 0.00 | 0.00 | 0.00 | 0.00 | 0.00 | 0.00 |
| Acetaldehyde | 68.33 | 79.20 | 78.09 | 78.09 | 1.11 | 78.09 |
| Acrolein | 1008.16 | 1168.50 | 1152.14 | 1152.14 | 16.36 | 1152.18 |
| Acetone | 2575.57 | 2982.64 | 2940.88 | 2940.88 | 41.76 | 2943.51 |
| Methanol | 0.00 | 0.00 | 0.00 | 0.00 | 0.00 | 0.00 |
| MA | 1886.65 | 2186.81 | 2156.20 | 2156.20 | 30.62 | 2156.18 |
| Water | 736412.06 | 853565.83 | 841615.91 | 841615.91 | 11949.92 | 841613.78 |
| MMA | 0.00 | 0.00 | 0.00 | 0.00 | 0.00 | 0.00 |
| MNPK | 0.00 | 0.00 | 0.00 | 0.00 | 0.00 | 0.00 |
| Toluene | 0.00 | 0.00 | 0.00 | 0.00 | 0.00 | 0.00 |
| Acetic acid | 162933.02 | 188853.63 | 186209.67 | 186209.67 | 2643.95 | 186209.17 |
| AA | 19188.92 | 22241.59 | 21930.21 | 21930.21 | 311.38 | 21930.20 |
| MAA | 1559530.00 | 1807630.00 | 1782320.00 | 1782320.00 | 25306.81 | 1782320.00 |
| Heavy Ends | 17336.94 | 20094.99 | 19813.66 | 19813.66 | 281.33 | 19813.65 |
| $H_2SO_4$ | 0.00 | 0.00 | 0.00 | 0.00 | 0.00 | 0.00 |
| Heavy Organics | 0.00 | 0.00 | 0.00 | 0.00 | 0.00 | 0.00 |
| N-butane | 0.00 | 0.00 | 0.00 | 0.00 | 0.00 | 0.00 |
| Formaldehyde | 0.00 | 0.00 | 0.00 | 0.00 | 0.00 | 0.00 |
| Ethyl acetate | 0.00 | 0.00 | 0.00 | 0.00 | 0.00 | 0.00 |
| N-hexane | 0.00 | 0.00 | 0.00 | 0.00 | 0.00 | 0.00 |
| Parameters | S50 | S52 | S54 | S56 | S58 | S60 |
| Temperature °C. | 67.00 | 48.78 | 55.06 | 55.06 | 55.06 | 60.72 |
| (°F.) | (152.60) | (119.80) | (131.10) | (131.10) | (131.10) | (141.30) |
| Pressure psi | 21.00 | 20.00 | 20.00 | 20.00 | 20.00 | 8.00 |
| Vapor Frac | 0.000 | 0.000 | 0.000 | 0.000 | 0.000 | 1.000 |
| Mole Flow lbmol/hr | 8881.03 | 18732.26 | 27613.29 | 11830.98 | 15782.31 | 11200.73 |
| Mass Flow lb/hr | 357391.98 | 635541.80 | 992933.78 | 425424.90 | 567508.87 | 398765.10 |
| Volume Flow cuft/hr | 6029.78 | 10559.56 | 16586.05 | 7106.33 | 9479.72 | 8929850.00 |
| Enthalpy MMBtu/hr | −1248.42 | −2554.80 | −3803.22 | −1629.50 | −2173.72 | −1549.04 |
| Mass Flow lb/hr | | | | | | |
| $N_2$ | 0.00 | 0.00 | 0.00 | 0.00 | 0.00 | 0.00 |
| CO | 0.10 | 0.12 | 0.22 | 0.09 | 0.12 | 5161.97 |
| $O_2$ | 0.29 | 0.35 | 0.64 | 0.28 | 0.37 | 11961.98 |
| $CO_2$ | 114.43 | 170.06 | 284.49 | 121.89 | 162.60 | 283956.42 |
| DME | 0.00 | 0.00 | 0.00 | 0.00 | 0.00 | 0.00 |
| Isobutene | 0.00 | 0.00 | 0.00 | 0.00 | 0.00 | 0.00 |
| Acetaldehyde | 9.76 | 15.63 | 25.39 | 10.88 | 14.51 | 121.34 |
| Acrolein | 144.02 | 202.42 | 346.44 | 148.44 | 198.01 | 927.24 |
| Acetone | 367.94 | 730.34 | 1098.28 | 470.56 | 627.72 | 1646.25 |
| Methanol | 0.00 | 0.00 | 0.00 | 0.00 | 0.00 | 0.00 |
| MA | 269.52 | 383.42 | 652.94 | 279.75 | 373.19 | 2973.91 |
| Water | 105201.72 | 253366.76 | 358568.48 | 153629.54 | 204938.94 | 68082.65 |
| MMA | 0.00 | 0.00 | 0.00 | 0.00 | 0.00 | 0.00 |
| MNPK | 0.00 | 0.00 | 0.00 | 0.00 | 0.00 | 0.00 |
| Toluene | 0.00 | 0.00 | 0.00 | 0.00 | 0.00 | 0.00 |
| Acetic acid | 23276.15 | 46415.41 | 69691.56 | 29859.52 | 39832.04 | 8550.94 |
| AA | 2741.27 | 3857.98 | 6599.25 | 2827.47 | 3771.79 | 91.37 |

TABLE II-continued

Stream Properties in Quench Distillation Subsystem

| | | | | | | |
|---|---|---|---|---|---|---|
| MAA | 222790.06 | 327095.40 | 549885.46 | 235599.77 | 314285.69 | 15291.03 |
| Heavy Ends | 2476.71 | 3303.94 | 5780.64 | 2476.73 | 3303.91 | 0.01 |
| $H_2SO_4$ | 0.00 | 0.00 | 0.00 | 0.00 | 0.00 | 0.00 |
| Heavy Organics | 0.00 | 0.00 | 0.00 | 0.00 | 0.00 | 0.00 |
| N-butane | 0.00 | 0.00 | 0.00 | 0.00 | 0.00 | 0.00 |
| Formaldehyde | 0.00 | 0.00 | 0.00 | 0.00 | 0.00 | 0.00 |
| Ethyl acetate | 0.00 | 0.00 | 0.00 | 0.00 | 0.00 | 0.00 |
| N-hexane | 0.00 | 0.00 | 0.00 | 0.00 | 0.00 | 0.00 |

| Parameters | S62 | S64 | S66 | S68 | S70 | S72 |
|---|---|---|---|---|---|---|
| Temperature ° C. | 54.89 | 51.61 | 51.61 | 114.72 | 36.00 | 32.22 |
| (° F.) | (130.80) | (124.90) | (124.90) | (238.50) | (95.00) | (90.00) |
| Pressure psi | 6.00 | 5.00 | 5.00 | 10.00 | 6.00 | 5.00 |
| Vapor Frac | 0.418 | 1.000 | 0.000 | 1.000 | 0.719 | 1.000 |
| Mole Flow lbmol/hr | 26983.04 | 11421.52 | 15561.52 | 11421.52 | 11421.52 | 8251.03 |
| Mass Flow lb/hr | 966273.97 | 403771.78 | 562502.19 | 403771.78 | 403771.78 | 330739.43 |
| Volume Flow cuft/hr | 11785500.00 | 14176300.00 | 9358.75 | 8517360.00 | 8113200.00 | 9690730.00 |
| Enthalpy MMBtu/hr | −3722.76 | −1575.49 | −2147.27 | −1561.63 | −1636.76 | −1229.23 |
| Mass Flow lb/hr | | | | | | |
| $N_2$ | 0.00 | 0.00 | 0.00 | 0.00 | 0.00 | 0.00 |
| CO | 5162.10 | 5162.00 | 0.09 | 5162.00 | 5162.00 | 5161.98 |
| $O_2$ | 11962.35 | 11962.07 | 0.28 | 11962.07 | 11962.07 | 11962.00 |
| $CO_2$ | 284119.01 | 283989.85 | 129.16 | 283989.85 | 283989.85 | 283948.96 |
| DME | 0.00 | 0.00 | 0.00 | 0.00 | 0.00 | 0.00 |
| Isobutene | 0.00 | 0.00 | 0.00 | 0.00 | 0.00 | 0.00 |
| Acetaldehyde | 135.85 | 123.80 | 12.05 | 123.80 | 123.80 | 120.23 |
| Acrolein | 1125.25 | 952.24 | 173.01 | 952.24 | 952.24 | 922.84 |
| Acetone | 2273.96 | 1727.79 | 546.17 | 1727.79 | 1727.79 | 1544.47 |
| Methanol | 0.00 | 0.00 | 0.00 | 0.00 | 0.00 | 0.00 |
| Pressure psi | 6.00 | 5.00 | 5.00 | 10.00 | 6.00 | 5.00 |
| MA | 3347.10 | 3026.54 | 320.56 | 3026.54 | 3026.54 | 2963.68 |
| Water | 273021.58 | 71619.15 | 201402.44 | 71619.15 | 71619.15 | 19658.54 |
| MMA | 0.00 | 0.00 | 0.00 | 0.00 | 0.00 | 0.00 |
| MNPK | 0.00 | 0.00 | 0.00 | 0.00 | 0.00 | 0.00 |
| Toluene | 0.00 | 0.00 | 0.00 | 0.00 | 0.00 | 0.00 |
| Acetic acid | 48382.98 | 9793.35 | 38589.62 | 9793.35 | 9793.35 | 1967.98 |
| AA | 3863.15 | 89.55 | 3773.60 | 89.55 | 89.55 | 5.20 |
| MAA | 329576.71 | 15325.42 | 314251.29 | 15325.42 | 15325.42 | 2483.56 |
| Heavy Ends | 3303.92 | 0.00 | 3303.92 | 0.00 | 0.00 | 0.00 |
| $H_2SO_4$ | 0.00 | 0.00 | 0.00 | 0.00 | 0.00 | 0.00 |
| Heavy Organics | 0.00 | 0.00 | 0.00 | 0.00 | 0.00 | 0.00 |
| N-butane | 0.00 | 0.00 | 0.00 | 0.00 | 0.00 | 0.00 |
| Formaldehyde | 0.00 | 0.00 | 0.00 | 0.00 | 0.00 | 0.00 |
| Ethyl acetate | 0.00 | 0.00 | 0.00 | 0.00 | 0.00 | 0.00 |
| N-hexane | 0.00 | 0.00 | 0.00 | 0.00 | 0.00 | 0.00 |

| Parameters | S74 | S76 | S78 | S80 | S82 |
|---|---|---|---|---|---|
| Temperature ° C. | 32.22 | 48.78 | 49.89 | 117.39 | 88.28 |
| (° F.) | (90.00) | (119.80) | (120.00) | (243.30) | (190.90) |
| Pressure psi | 5.00 | 5.00 | 49.00 | 57.00 | 10.00 |
| Vapor Frac | 0.000 | 0.000 | 1.000 | 0.000 | 0.003 |
| Mole Flow lbmol/hr | 3170.49 | 18732.26 | 8251.03 | 1056.47 | 2065.27 |
| Mass Flow lb/hr | 73032.34 | 635541.80 | 330739.43 | 22230.00 | 62826.27 |
| Volume Flow cuft/hr | 1197.85 | 10559.31 | 1024360.00 | 401.47 | 5840.29 |
| Enthalpy MMBtu/hr | −407.53 | −2554.84 | −1227.70 | −130.65 | −272.46 |
| Mass Flow lb/hr | | | | | |
| $N_2$ | 0.00 | 0.00 | 0.00 | 0.00 | 0.00 |
| CO | 0.02 | 0.12 | 5161.98 | 0.00 | 0.01 |
| $O_2$ | 0.07 | 0.35 | 11962.00 | 0.00 | 0.03 |
| $CO_2$ | 40.89 | 170.06 | 283948.96 | 0.00 | 13.00 |
| DME | 0.00 | 0.00 | 0.00 | 0.00 | 0.00 |
| Isobutene | 0.00 | 0.00 | 0.00 | 0.00 | 0.00 |
| Acetaldehyde | 3.57 | 15.63 | 120.23 | 0.28 | 1.39 |
| Acrolein | 29.40 | 202.42 | 922.84 | 0.85 | 17.21 |
| Acetone | 183.33 | 730.34 | 1544.47 | 37.28 | 79.04 |
| Methanol | 0.00 | 0.00 | 0.00 | 0.00 | 0.00 |
| MA | 62.86 | 383.42 | 2963.68 | 0.00 | 30.62 |
| Water | 51960.60 | 253366.76 | 19658.54 | 17966.24 | 29916.16 |
| MMA | 0.00 | 0.00 | 0.00 | 0.00 | 0.00 |
| MNPK | 0.00 | 0.00 | 0.00 | 0.00 | 0.00 |
| Toluene | 0.00 | 0.00 | 0.00 | 0.00 | 0.00 |
| Acetic acid | 7825.37 | 46415.41 | 1967.98 | 1873.72 | 4517.67 |
| AA | 84.35 | 3857.98 | 5.20 | 5.10 | 316.49 |
| MAA | 12841.86 | 327095.40 | 2483.56 | 2346.52 | 27653.33 |

TABLE II-continued

Stream Properties in Quench Distillation Subsystem

| | | | | | |
|---|---:|---:|---:|---:|---:|
| Heavy Ends | 0.00 | 3303.94 | 0.00 | 0.00 | 281.33 |
| $H_2SO_4$ | 0.00 | 0.00 | 0.00 | 0.00 | 0.00 |
| Heavy Organics | 0.00 | 0.00 | 0.00 | 0.00 | 0.00 |
| N-butane | 0.00 | 0.00 | 0.00 | 0.00 | 0.00 |
| Formaldehyde | 0.00 | 0.00 | 0.00 | 0.00 | 0.00 |
| Ethyl acetate | 0.00 | 0.00 | 0.00 | 0.00 | 0.00 |
| N-hexane | 0.00 | 0.00 | 0.00 | 0.00 | 0.00 |

TABLE III

Stream Properties in Absorber/Stripper Subsystem

| Parameters | S84 | S86 | S88 | S96 | S98 | S100 |
|---|---:|---:|---:|---:|---:|---:|
| Temperature ° C. | 36.28 | 36.28 | 259.78 | 117.39 | 117.39 | 117.39 |
| (° F.) | (97.30) | (97.30) | (499.60) | (243.30) | (243.30) | (243.30) |
| Pressure psi | 48.00 | 53.00 | 34.00 | 27.00 | 27.00 | 57.00 |
| Vapor Frac | 0.000 | 0.000 | 1.000 | 0.000 | 0.000 | 0.000 |
| Mole Flow lbmol/hr | 54439.25 | 54439.25 | 0.24 | 54177.95 | 54177.95 | 54177.95 |
| Mass Flow lb/hr | 1151940.00 | 1151940.00 | 10.00 | 1140000.00 | 1140000.00 | 1140000.00 |
| Volume Flow cuft/hr | 18937.37 | 18937.45 | 70.95 | 20587.33 | 20587.33 | 20588.25 |
| Enthalpy MMBtu/hr | −6879.53 | −6879.51 | −0.04 | −6699.93 | −6699.93 | −6699.79 |
| Mass Flow lb/hr | | | | | | |
| $N_2$ | 0.00 | 0.00 | 0.00 | 0.00 | 0.00 | 0.00 |
| CO | 3.34 | 3.34 | 0.00 | 0.00 | 0.00 | 0.00 |
| $O_2$ | 10.08 | 10.08 | 0.56 | 0.00 | 0.00 | 0.00 |
| $CO_2$ | 5484.75 | 5484.75 | 9.36 | 0.03 | 0.03 | 0.03 |
| DME | 0.00 | 0.00 | 0.00 | 0.00 | 0.00 | 0.00 |
| Isobutene | 0.00 | 0.00 | 0.00 | 0.00 | 0.00 | 0.00 |
| Acetaldehyde | 132.29 | 132.29 | 0.00 | 14.27 | 14.27 | 14.27 |
| Acrolein | 957.90 | 957.90 | 0.00 | 43.79 | 43.79 | 43.79 |
| Acetone | 3366.66 | 3366.66 | 0.00 | 1911.95 | 1911.95 | 1911.95 |
| Methanol | 0.00 | 0.00 | 0.00 | 0.00 | 0.00 | 0.00 |
| MA | 2963.68 | 2963.68 | 0.00 | 0.00 | 0.00 | 0.00 |
| Water | 922217.22 | 922217.22 | 0.08 | 921345.66 | 921345.66 | 921345.66 |
| MMA | 0.00 | 0.00 | 0.00 | 0.00 | 0.00 | 0.00 |
| MNPK | 0.00 | 0.00 | 0.00 | 0.00 | 0.00 | 0.00 |
| Toluene | 0.00 | 0.00 | 0.00 | 0.00 | 0.00 | 0.00 |
| Acetic acid | 96130.36 | 96130.36 | 0.00 | 96088.13 | 96088.13 | 96088.13 |
| AA | 261.75 | 261.75 | 0.00 | 261.70 | 261.70 | 261.70 |
| MAA | 120407.30 | 120407.30 | 0.00 | 120334.47 | 120334.47 | 120334.47 |
| Heavy Ends | 0.00 | 0.00 | 0.00 | 0.00 | 0.00 | 0.00 |
| $H_2SO_4$ | 0.00 | 0.00 | 0.00 | 0.00 | 0.00 | 0.00 |
| Heavy Organics | 0.00 | 0.00 | 0.00 | 0.00 | 0.00 | 0.00 |
| N-butane | 0.00 | 0.00 | 0.00 | 0.00 | 0.00 | 0.00 |
| Formaldehyde | 0.00 | 0.00 | 0.00 | 0.00 | 0.00 | 0.00 |
| Ethyl acetate | 0.00 | 0.00 | 0.00 | 0.00 | 0.00 | 0.00 |
| N-hexane | 0.00 | 0.00 | 0.00 | 0.00 | 0.00 | 0.00 |

| Parameters | S102 | S104 | S106 | S108 | S110 | S112 |
|---|---:|---:|---:|---:|---:|---:|
| Temperature ° C. | 117.39 | 21.11 | 21.11 | 21.1 | 15.56 | 17.22 |
| (° F.) | (243.30) | (70.00) | (70.00) | (70.00) | (60.00) | (63.00) |
| Pressure psi | 57.00 | 49.00 | 49.00 | 49.00 | 47.00 | 43.00 |
| Vapor Frac | 0.000 | 0.000 | 0.000 | 0.000 | 0.000 | 1.000 |
| Mole Flow lbmol/hr | 53121.48 | 53121.52 | 45153.29 | 7968.23 | 7968.23 | 6930.93 |
| Mass Flow lb/hr | 1117770.00 | 1117770.00 | 950104.50 | 167665.50 | 167665.50 | 296470.63 |
| Volume Flow cuft/hr | 20186.78 | 18088.32 | 15375.07 | 2713.25 | 2698.10 | 887191.07 |
| Enthalpy MMBtu/hr | −6569.14 | −6736.03 | −5725.63 | −1010.40 | −1011.75 | −1085.15 |
| Mass Flow lb/hr | | | | | | |
| $N_2$ | 0.00 | 0.00 | 0.00 | 0.00 | 0.00 | 0.00 |
| CO | 0.00 | 0.00 | 0.00 | 0.00 | 0.00 | 5159.53 |
| $O_2$ | 0.00 | 0.00 | 0.00 | 0.00 | 0.00 | 11949.69 |
| $CO_2$ | 0.03 | 0.03 | 0.02 | 0.00 | 0.00 | 278362.13 |
| DME | 0.00 | 0.00 | 0.00 | 0.00 | 0.00 | 0.00 |
| Isobutene | 0.00 | 0.00 | 0.00 | 0.00 | 0.00 | 0.00 |
| Acetaldehyde | 13.99 | 13.98 | 11.89 | 2.10 | 2.10 | 1.93 |
| Acrolein | 42.93 | 42.91 | 36.47 | 6.44 | 6.44 | 7.91 |
| Acetone | 1874.67 | 1873.32 | 1592.32 | 281.00 | 281.00 | 51.40 |
| Methanol | 0.00 | 0.00 | 0.00 | 0.00 | 0.00 | 0.00 |
| MA | 0.00 | 0.00 | 0.00 | 0.00 | 0.00 | 0.00 |
| Water | 903379.42 | 903380.52 | 767873.45 | 135507.08 | 135507.08 | 821.55 |
| MMA | 0.00 | 0.00 | 0.00 | 0.00 | 0.00 | 0.00 |

TABLE III-continued

Stream Properties in Absorber/Stripper Subsystem

| | | | | | | |
|---|---|---|---|---|---|---|
| MNPK | 0.00 | 0.00 | 0.00 | 0.00 | 0.00 | 0.00 |
| Toluene | 0.00 | 0.00 | 0.00 | 0.00 | 0.00 | 0.00 |
| Acetic acid | 94214.41 | 94214.52 | 80082.34 | 14132.18 | 14132.18 | 52.11 |
| AA | 256.60 | 256.60 | 218.11 | 38.49 | 38.49 | 0.05 |
| MAA | 117987.95 | 117988.12 | 100289.90 | 17698.22 | 17698.22 | 64.34 |
| Heavy Ends | 0.00 | 0.00 | 0.00 | 0.00 | 0.00 | 0.00 |
| $H_2SO_4$ | 0.00 | 0.00 | 0.00 | 0.00 | 0.00 | 0.00 |
| Heavy Organics | 0.00 | 0.00 | 0.00 | 0.00 | 0.00 | 0.00 |
| N-butane | 0.00 | 0.00 | 0.00 | 0.00 | 0.00 | 0.00 |
| Formaldehyde | 0.00 | 0.00 | 0.00 | 0.00 | 0.00 | 0.00 |
| Ethyl acetate | 0.00 | 0.00 | 0.00 | 0.00 | 0.00 | 0.00 |
| N-hexane | 0.00 | 0.00 | 0.00 | 0.00 | 0.00 | 0.00 |

TABLE IV

Stream Properties in Stripper Gas Subsystem

| Parameters | S114 | S115 | S116 | S118 | S120 | S122 |
|---|---|---|---|---|---|---|
| Temperature ° C. | 141.61 | 161.89 | 20 | 364.94 | 260 | 259.78 |
| (° F.) | (286.90) | (323.40) | (68.00) | (688.90) | (500.00) | (499.60) |
| Pressure psi | 45.00 | 45.00 | 43.00 | 38.00 | 34.00 | 34.00 |
| Vapor Frac | 1.000 | 0.408 | 0.998 | 1.000 | 1.000 | 1.000 |
| Mole Flow lbmol/hr | 10.17 | 11.49 | 6952.59 | 7289.34 | 7289.34 | 695.83 |
| Mass Flow lb/hr | 533.14 | 1066.72 | 298070.50 | 310570.50 | 310570.50 | 29646.76 |
| Volume Flow cuft/hr | 1758.30 | 821.48 | 897045.56 | 2362510.00 | 2202390.00 | 210329.19 |
| Enthalpy MMBtu/hr | −0.76 | −1.55 | −1087.46 | −1087.48 | −1102.51 | −105.24 |
| Mass Flow lb/hr | | | | | | |
| $N_2$ | 0.00 | 0.00 | 0.00 | 0.00 | 0.00 | 0.00 |
| CO | 0.01 | 0.00 | 5159.54 | 0.00 | 0.00 | 0.00 |
| $O_2$ | 0.03 | 0.00 | 11949.72 | 17263.11 | 17263.11 | 1647.92 |
| $CO_2$ | 13.00 | 0.00 | 278375.13 | 290706.98 | 290706.98 | 27750.61 |
| DME | 157.70 | 0.00 | 157.70 | 0.00 | 0.00 | 0.00 |
| Isobutene | 0.00 | 0.00 | 0.00 | 0.00 | 0.00 | 0.00 |
| Acetaldehyde | 1.37 | 0.02 | 3.32 | 0.00 | 0.00 | 0.00 |
| Acrolein | 16.99 | 0.15 | 25.05 | 0.00 | 0.00 | 0.00 |
| Acetone | 74.16 | 1.60 | 127.16 | 0.00 | 0.00 | 0.00 |
| Methanol | 28.20 | 0.00 | 28.20 | 0.00 | 0.00 | 0.00 |
| MA | 30.43 | 0.15 | 30.58 | 0.00 | 0.00 | 0.00 |
| Water | 24.20 | 3.61 | 849.36 | 2600.39 | 2600.39 | 248.23 |
| MMA | 0.06 | 0.00 | 0.06 | 0.00 | 0.00 | 0.00 |
| MNPK | 0.00 | 0.00 | 0.00 | 0.00 | 0.00 | 0.00 |
| Toluene | 83.08 | 0.02 | 83.10 | 0.00 | 0.00 | 0.00 |
| Acetic acid | 13.98 | 29.00 | 95.08 | 0.00 | 0.00 | 0.00 |
| AA | 0.00 | 288.89 | 288.93 | 0.00 | 0.00 | 0.00 |
| MAA | 0.02 | 45.07 | 109.43 | 0.00 | 0.00 | 0.00 |
| Heavy Ends | 0.00 | 281.35 | 281.35 | 0.00 | 0.00 | 0.00 |
| $H_2SO_4$ | 0.00 | 0.00 | 0.00 | 0.00 | 0.00 | 0.00 |
| Heavy Organics | 0.00 | 0.00 | 0.00 | 0.00 | 0.00 | 0.00 |
| N-butane | 0.00 | 0.00 | 0.00 | 0.00 | 0.00 | 0.00 |
| Formaldehyde | 0.00 | 0.01 | 0.01 | 0.01 | 0.01 | 0.00 |
| Ethyl acetate | 6.32 | 4.30 | 10.61 | 0.00 | 0.00 | 0.00 |
| N-hexane | 83.60 | 412.56 | 496.15 | 0.00 | 0.00 | 0.00 |

The overall separation efficiencies of the columns utilized in this system are tabulated in Table V.

TABLE V

Separation Efficiencies
Product Losses as Percentage of Total Product Made

| Separation Unit | Product Loss |
|---|---|
| Quench Column | 0.14 |
| Absorber Column | 0.23 |
| Stripper Column | 0.05 |
| Overall | 0.42 |

All references cited herein are incorporated by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

I claim:

1. A methacrylic acid production system comprising:
   an oxidation subsystem adapted to oxidize a feed stream including isobutene and an methacrolein (MA) recycle stream into a hot oxidized stream including MA, methacrylic acid (MAA) and acetic acid (AA);
   a quench/distillation subsystem adapted to quench the hot oxidized stream with an amount of a quench stream sufficient to reduce the hot oxidized stream from an initial temperature of about 280° C. to a final temperature below about 75° C. instantaneously or near instantaneously and to distillatively form an MAA rich bottoms stream including a major portion of the AA produced in the system and an MA rich overhead stream;

an MAA recycle subsystem adapted to form a first MAA product stream, the quench stream and an MAA rich overhead recycle stream;

an MA overhead separation and recycle subsystem adapted to separate an MA rich overhead stream into an MA rich vapor stream and an MA lean recycle stream;

an absorber/stripper system adapted to recover MAA and AA present in the MA rich vapor stream and to produce the MA recycle stream, a second MAA product stream and a lights waste stream, and an optionally a stripper gas system adapted to form a stripper gas stream formed by incinerating an incineration stream including the lights waste stream.

2. The system of claim 1, wherein the oxidation subsystem comprises:
at least one oxidation reactor having a feed stream inlet and a oxidize stream outlet.

3. The system of claim 1, wherein the oxidation subsystem comprises:
a first oxidation reactor having an inlet, an outlet and a mixed metal oxide catalyst adapted to oxidize the feed stream to form an MA rich oxidized stream, and
a second oxidation reactor having an inlet, an outlet and a heteropolyacid catalyst adapted to oxidize the MA rich oxidized stream to form the hot oxidized stream.

4. The system of claim 1, wherein the quench/distillation subsystem comprises:
a quench/distillation (Q/D) column having:
a sump portion including:
a crude oxidized stream inlet, and
a quench stream inlet,
a bottoms stream outlet,
an overhead stream outlet, and
a reflux stream inlet,
where the quench/distillation subsystem is adapted to feed the quench stream and the hot oxidized stream to the Q/D column at a ratio of a mass flow of the quench stream to a mass flow of the hot oxidized stream is at least 5:1.

5. The system of claim 1, wherein the MAA recycle subsystem comprises:
a pump to increase a pressure of the MAA rich bottoms stream,
a dividing valve adapted to divide the MAA rich bottoms stream into the recycle stream and an MAA product stream,
a first heat exchanger adapted to cool the recycle stream,
a second dividing valve adapted to divide the recycle stream into the quench stream and the MAA rich overhead recycle stream;
a first combining valve adapted to combine the MAA rich overhead recycle stream and a pressurized MA lean recycle stream to form a combined stream, and
a third dividing valve adapted to divide the combined stream into a reflux stream and a venturi valve stream, where the reflux stream is fed into the reflux stream inlet of the Q/D column.

6. The system of claim 5, wherein the MA overhead separation and recycle subsystem including:
a venturi adapted to remove fine particulate material from the MA rich overhead stream using the venturi valve stream,
a first separator adapted to separate the MA rich overhead stream into a first vapor stream and first liquid stream,
a compressor to increase the pressure of the first vapor stream,
a second heat exchanger adapted to cool the first vapor stream to form a partially condensed stream,
a second separator adapted to separate the partially condensed stream into the MA rich vapor stream and a second liquid stream,
a second combining valve adapted to combine the first and second liquid streams to form the MA lean recycle stream, and
pump to increase a pressure of the MA lean recycle stream, and
a second compressor to increase a pressure of the MA rich vapor stream.

7. The system of claim 1, wherein the absorber/stripper system comprises:
an absorber column adapted to receive the pressurized MA rich vapor stream and a MAA rich absorber stream forming an absorber bottoms stream; and
a stripper column adapted to receive the absorber bottoms stream, a reboiler stream, and a stripper gas stream to produce the absorber stream, the MA recycle stream, and a second MAA product stream, which is combined with the first MAA product stream.

8. The system of claim 1, wherein the stripper gas system comprising:
an incinerator adapted to incinerating absorber column overheads into a stripper gas stream used in a stripper column to strip unreacted MA for recycle to the oxidation subsystem.

9. The system of claim 1, wherein the Q/D column further comprises:
an oxidized stream injection unit adapted to inject the hot oxidized stream into the Q/D column above a liquid layer in the Q/D column, and
a quench stream injection unit located above the oxidized stream injection unit to inject the quench stream so that it quenches the hot oxidized stream.

10. The system of claim 1, wherein the absorber/stripper system comprises:
an absorber column including:
a lower side port for receiving the MA rich vapor stream into the absorber column,
a top side port for receiving a first absorbent stream into the absorber column,
an upper side port for receiving a second absorbent stream into the absorber column,
a bottom port for withdrawing an absorber bottoms stream from the absorber column,
a top port for withdrawing a waste overhead stream from of the absorber column,
a stripper column including:
a top input port for receiving the absorber bottoms stream into the stripper column, a lower side port for receiving a stripper gas stream into the stripper column, a top output port for withdrawing an overhead stream comprising all or substantially all of the MA from the stripper column, a bottom port for withdrawing a stripper bottoms stream from of the stripper column, and a bottom side port for recycling a first stripper bottoms substream through a reboiler into the stripper column, a first splitter valve for forming the first stripper bottoms substream and a second stripper bottoms substream, a second splitter valve for taking a small split stream from the second stripper bottoms substream for MAA and AA recovery, and for recycling the balance of the stripper bottoms stream as the absorbent stream for the absorber column, where a mass ratio of the split stream to the remaining stripper bottoms is governed by:

$$Y = C_1 + C_2 * X$$

where $C_1$ and $C_2$ are constants, Y is a ratio of mass flow in the split stream to the remaining stripper bottoms mass flow, and X is the mass flow of the remaining stripper bottoms, where a mass ratio of the split stream to the remaining stripper bottoms is governed by:

$$Y = C_1 + C_2 * X$$

where $C_1$ and $C_2$ are constants, Y is a ratio of mass flow in the split stream to the remaining stripper bottoms mass flow, and X is the mass flow of the remaining stripper bottoms.

11. A methacrylic acid production system comprising:
an oxidation subsystem including:
at least one oxidation reactor having a feed stream inlet and an oxidized stream outlet,
where the oxidation subsystem is adapted to oxidize a feed stream including isobutene into a hot oxidized stream including methacrolein (MA), methacrylic acid (MAA) and acetic acid (AA);
a quench/distillation subsystem including:
a column having:
a sump portion including:
a crude oxidized stream inlet, and
a quench stream inlet,
a bottoms stream outlet,
an overhead stream outlet, and
a reflux stream inlet,
where the quench/distillation subsystem is adapted to instantaneously or near instantaneously quench the hot oxidized stream from an initial temperature of about 280° C. to a final temperature below about 75° C. and to separate a column contents into an MAA rich bottoms stream including most of the AA produced in the system and an MA rich overhead stream, an MAA recycle subsystem including:
a pump to increase a pressure of the MAA rich bottoms stream,
a dividing valve adapted to divide the MAA rich bottoms stream into the recycle stream and an MAA product stream,
a first heat exchanger adapted to cool the recycle stream, a second dividing valve adapted to divide the recycle stream into the quench stream and an overhead MAA recycle stream;
a first combining valve adapted to combine the overhead MAA recycle stream and a pressurized liquid overhead stream to form a combined stream,
a third dividing valve adapted to divide the combined stream into a reflux stream and a venturi valve stream, where the reflux stream is fed into the reflux stream inlet of the column,
an MA overhead separation and recycle subsystem including:
a venturi adapted to remove fine particulate material from the MA rich overhead stream using the MA rich overhead stream and the venturi valve stream,
a first separator adapted to separate the MA rich overhead stream into a first vapor stream and first liquid stream,
a compressor to increase the pressure of the vapor stream,
a second heat exchanger adapted to cool the vapor stream to form a partially condensed stream,
a second separator adapted to separate the partially condensed stream into a second vapor stream and a second liquid stream,
a second combining valve adapted to combine the first and second liquid streams to form a combined liquid stream, and
a pump to increase a pressure of the combined liquid stream,
a second compressor to increase a pressure of the second vapor stream,
an absorber/stripper system including:
an absorber column adapted to receive the second vapor stream to remove unconverted MA for recycle to the oxidation subsystem and
a stripper column adapted to produce an MA recycle stream, an absorber stream and a second MAA rich product stream, which is combined with the MAA product stream; and
an optionally a stripper gas system including:
an incinerator adapted to incinerate absorber column overheads into a stripper gas stream used in a stripper column to strip unreacted MA for recycle to the oxidation subsystem.

12. The system of claim 11, wherein:
the absorber column including:
a lower side port for receiving the MA rich vapor stream into the absorber column,
a top side port for receiving a first absorbent stream into the absorber column,
an upper side port for receiving a second absorbent stream into the absorber column,
a bottom port for withdrawing an absorber bottoms stream from the absorber column,
a top port for withdrawing a waste overhead stream from of the absorber column,
the stripper column including:
a top input port for receiving the absorber bottoms stream into the stripper column, a lower side port for receiving a stripper gas stream into the stripper column, a top output port for withdrawing an overhead stream comprising all or substantially all of the MA from the stripper column, a bottom port for withdrawing a stripper bottoms stream from of the stripper column, and a bottom side port for recycling a first stripper bottoms substream through a reboiler into the stripper column, and wherein the absorber/stripper system further includes:

a first splitter valve for forming the first stripper bottoms substream and a second stripper bottoms substream, a second splitter valve for taking a small split stream from the second stripper bottoms substream for MAA and AA recovery, and for recycling the balance of the stripper bottoms stream as the absorbent stream for the absorber column, where a mass ratio of the split stream to the remaining stripper bottoms is governed by:

$$Y = C_1 + C_2 * X$$

where $C_1$ and $C_2$ are constants, Y is a ratio of mass flow in the split stream to the remaining stripper bottoms mass flow, and X is the mass flow of the remaining stripper bottoms, where a mass ratio of the split stream to the remaining stripper bottoms is governed by:

$$Y = C_1 + C_2 * X$$

where $C_1$ and $C_2$ are constants, Y is a ratio of mass flow in the split stream to the remaining stripper bottoms mass flow, and X is the mass flow of the remaining stripper bottoms.

\* \* \* \* \*